United States Patent
Pohl et al.

(10) Patent No.: US 8,724,097 B2
(45) Date of Patent: May 13, 2014

(54) OPTICAL HAZARD AVOIDANCE AND METHOD

(75) Inventors: Kenneth Randall Pohl, Largo, FL (US); Alan Ray Ford, Largo, FL (US); Robert Douglas Waterbury, Largo, FL (US); Darius Vunck, Largo, FL (US); Edwin L. Dottery, Largo, FL (US)

(73) Assignee: Alakai Defense Systems, Inc., Largo, FL (US)

( * ) Notice: Subject to any disclaimer, the term of this patent is extended or adjusted under 35 U.S.C. 154(b) by 42 days.

(21) Appl. No.: 13/470,679

(22) Filed: May 14, 2012

(65) Prior Publication Data

US 2013/0128261 A1    May 23, 2013

Related U.S. Application Data

(63) Continuation of application No. PCT/US2012/037679, filed on May 12, 2012.

(60) Provisional application No. 61/485,473, filed on May 12, 2001, provisional application No. 61/610,359, filed on Mar. 13, 2012.

(51) Int. Cl.
| | |
|---|---|
| G01J 3/00 | (2006.01) |
| G01J 3/44 | (2006.01) |
| G01J 1/32 | (2006.01) |
| H01S 3/13 | (2006.01) |
| H01S 3/00 | (2006.01) |

(52) U.S. Cl.
USPC .......... 356/51; 356/301; 250/205; 372/29.01; 372/29.014; 372/33

(58) Field of Classification Search
None
See application file for complete search history.

(56) References Cited

U.S. PATENT DOCUMENTS

| | | |
|---|---|---|
| 4,285,588 A | 8/1981 | Mir |
| 4,299,464 A | 11/1981 | Cushman |
| 4,945,239 A | 7/1990 | Wist et al. |

(Continued)

FOREIGN PATENT DOCUMENTS

| | | | |
|---|---|---|---|
| EP | 2381156 A1 | * | 10/2011 |
| WO | WO 2010046822 A1 | * | 4/2010 |

OTHER PUBLICATIONS

American National Standard for Safe Use of Lasers Outdoors, ANSI Z136.6-2005, copyright 2005 by Laser Institute of America, ISBN: #0-912035-66-8.

(Continued)

*Primary Examiner* — Gordon J Stock, Jr.
(74) *Attorney, Agent, or Firm* — Christopher Paradies; Paradies Law P.A.

(57) ABSTRACT

A source of light that could cause ocular damage within a given range from the source of light, such as a first laser, is accompanied by an optical hazard avoidance device, such as a second laser, that stimulates voluntary, involuntary, or both voluntary and involuntary responses, either physiological or behavioral or both physiological and behavioral, within one or more hazard zones, such as by inducing gaze aversion within the viewer. For example, a visible laser beam induces gaze aversion, pupil contraction or a combination of gaze aversion and pupil contraction, reducing the dose rate or exposure of the ocular tissue to damaging radiation from a primary source. In one example, the primary source is a UV Raman detector and the visible laser beam is selected to induce gaze aversion.

22 Claims, 18 Drawing Sheets

(56) References Cited

U.S. PATENT DOCUMENTS

| | | | |
|---|---|---|---|
| 5,685,636 A * | 11/1997 | German | 362/259 |
| 5,946,092 A | 8/1999 | DeFreez et al. | |
| 6,190,022 B1 | 2/2001 | Tocci et al. | |
| 6,208,270 B1 | 3/2001 | Dunn | |
| 6,270,467 B1 | 8/2001 | Yee | |
| 6,593,582 B2 * | 7/2003 | Lee et al. | 250/458.1 |
| 6,799,868 B2 * | 10/2004 | Brown et al. | 362/259 |
| 7,133,123 B1 | 11/2006 | Lei et al. | |
| 7,180,426 B2 | 2/2007 | Rubtsov | |
| 7,239,655 B2 * | 7/2007 | Casazza | 372/36 |
| 7,500,763 B2 | 3/2009 | Rubtsov | |
| 7,695,141 B2 | 4/2010 | Hara et al. | |
| 7,762,964 B2 * | 7/2010 | Slatkine | 601/7 |
| 8,125,627 B2 | 2/2012 | Dottery et al. | |
| 8,203,698 B2 * | 6/2012 | Meyers et al. | 356/5.01 |
| 8,389,919 B2 * | 3/2013 | Ziemkowski et al. | 250/205 |
| 2006/0238757 A1 | 10/2006 | Silcott | |
| 2007/0045257 A1 | 3/2007 | Moor et al. | |
| 2007/0049910 A1 * | 3/2007 | Altshuler et al. | 606/9 |
| 2007/0274353 A1 * | 11/2007 | Hauck et al. | 372/9 |
| 2008/0192232 A1 | 8/2008 | Ninomiya et al. | |
| 2009/0086489 A1 * | 4/2009 | Scott et al. | 362/259 |
| 2009/0299440 A9 * | 12/2009 | Slatkine | 607/89 |
| 2010/0177929 A1 * | 7/2010 | Kurtz et al. | 382/103 |
| 2012/0093504 A1 * | 4/2012 | Aronson et al. | 398/38 |
| 2012/0206922 A1 * | 8/2012 | Feklistov et al. | 362/311.12 |
| 2013/0016514 A1 * | 1/2013 | Stacey et al. | 362/253 |
| 2013/0293882 A1 * | 11/2013 | Dottery et al. | 356/301 |

OTHER PUBLICATIONS

American National Standard for Safe Use of Lasers, ANSI Z136.1-2007, Copyright 2007 by Laser Institute of America.

* cited by examiner

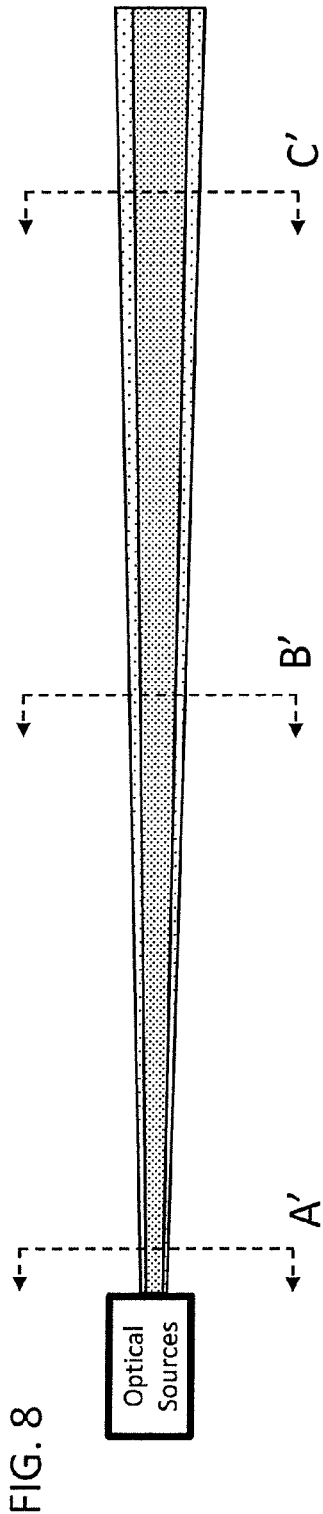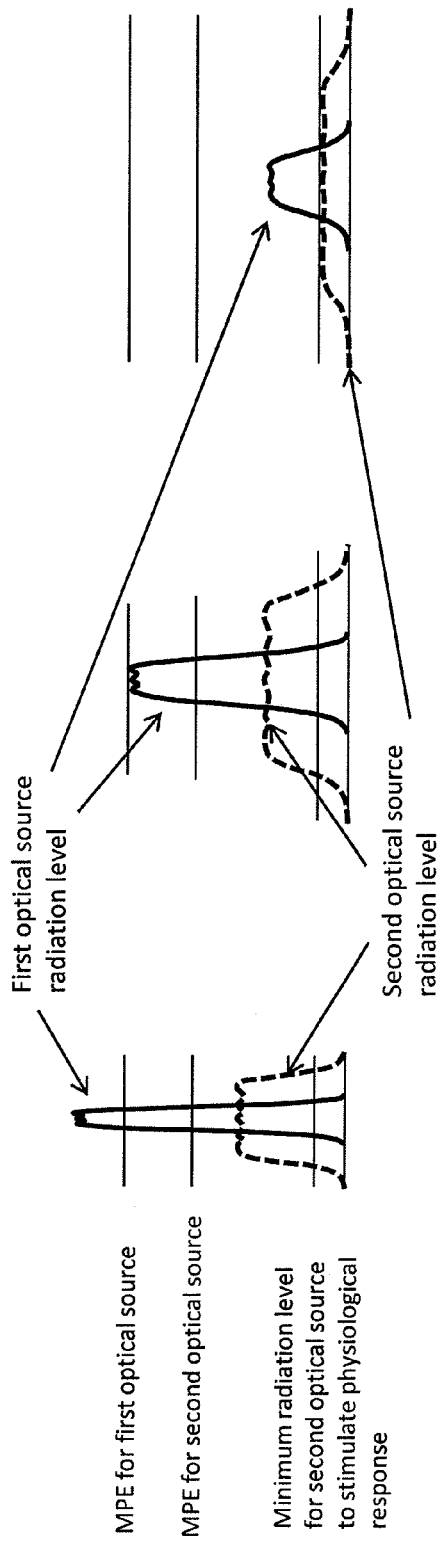
FIG. 8
FIG. 8A
FIG. 8B
FIG. 8C

OPTICAL HAZARD AVOIDANCE AND METHOD

REFERENCE TO RELATED APPLICATIONS

This application is a continuation of PCT/US12/37679 filed May 12, 2012 which claims the benefit of U.S. provisional application No. 61/485,473 filed May 12, 2011 and U.S. provisional application No. 61/610,359 filed Mar. 13, 2012 the disclosures of which are hereby incorporated herein by reference in their entirety.

FIELD OF THE INVENTION

The field relates to devices for prevention or mitigation of optical damage to the cornea and retina by exposure to an optical hazard such as a beam from a laser.

BACKGROUND

ANSI Z136.1-2007 discloses known and accepted methods for preventing and mitigating hazards caused by lasers to vision. The cornea and retina are especially vulnerable to damage in humans and animals from laser sources having frequencies with visible and not visible wavelength. In some instance, laser beams that are not visible are more dangerous than those in the visible range, the person or animal does not see the beam and cannot know to react to avoid damage. Visible beams of sufficient intensity can still cause damage if a person does not avert the eyes or blink, but a person may be subject to sustained exposure to an invisible beam that can cause damage over a longer period of time if the person stares into the beam with no knowledge of its existence.

In practice, engineering and safety controls prevent operation of an optical hazard or block the optical hazard from causing damage outside of a confined area or within a hazardous range. Even highly coherent laser beams diverge and attenuate over distances. Beams and sources with greater divergence attenuate that much more rapidly with distance from the source. Therefore, in some cases, an optical hazard may be limited to a comparatively short range, beyond which, even lengthy exposures will not cause any lasting damage.

Administrative and procedural controls are good practices generally adopted when use of potentially hazardous conditions could be caused by an optical hazard of some type. These practices may mitigate exposure when engineering and safety controls fail, for example, or when engineering and safety controls are impractical, such as in field use of lasers for targeting, detection, distance measuring and the like. These can include the use of special eyewear, films and filters and procedures for clearing a down range area of personnel prior to the use of optical hazards.

U.S. Pat. Nos. 7,500,763; 7,180,426; and 6,190,022 use a light source comprising a laser and/or LED's, with or without a range finder, to incapacitate individuals within range of the laser and/or LED's. These systems have a range finder or take other precautions to avoid a threshold exposure that would exceed a permissible exposure threshold that could cause permanent damage. While these devices are designed to merely temporarily disorient and incapacitate, use of these potentially hazardous optical devices is not allowed due to the possibility that such devices might cause temporary or permanent ocular damage, beyond the desired effect of mere temporary disorientation and incapacity. Rangefinders and the like are not 100% effective in detecting humans and animals within a danger zone, and approval for use of such devices is likely to be limited to devices that are limited to very modest effects, such as the light from flash bulbs and the like.

U.S. patent application Ser. No. 11/215,777 discloses a system for the purpose of preventing ocular damage from a laser using a sensor for sensing the position of a hand and a control for controlling the operation of the laser based on that position. This has the advantage of being able to prevent operation of the laser if the position of the hand is not in a safe location, but it has the disadvantage of being limited to a known user. The system is not capable of tracking the locations of unknown humans and animals that could stray into an optical hazard zone.

U.S. Pat. No. 6,270,467 discloses a system, device and method or preventing computer vision syndrome (CVS) using a means of reminding a particular computer user to blink, periodically, preventing excessive drying of the eyes.

U.S. Pat. No. 7,695,141 discloses a system using a stimulus light source projected to the retina of an ocular fundus under examination to stimulate the retina in a localized fashion to generate a bioelectrical signal from the retina, assuring a reliable local electroretinogram. The device is limited to an exam of a particular patient and cannot cause an avoidance response in the patient or others.

U.S. Pat. No. 4,299,464 discloses a method and device for utilizing a light source to stimulate an optical response to reduce or prevent "red eye" in flash photography. U.S. Pat. No. 4,285,588 discloses a method and device for reducing the incidence of eye closure during flash photography utilizing a pre-flash to cause the subject or subjects to blink prior to the opening of the shutter and a second flash. While this disclosure teaches the stimulation of an involuntary response, the pre-flash results in exposure of the eye to a flash rather than avoidance of a flash.

None of the known methods for preventing or mitigating damage from optical hazards uses stimulated physiological responses induced by a second laser or other optical hazard avoidance device in order to avoid or mitigate optical damage within a hazard zone of a first laser.

SUMMARY

An optical hazard avoidance device forces a physiologic response in a person or animal ("viewer") that mitigates the optical exposure of the viewer to a particular optical hazard that would otherwise possibly cause temporary or permanent ocular damage, such as corneal or retinal damage. The device stimulates an involuntary and/or voluntary avoidance response.

In one example, a source of light that could cause ocular damage within a given range from the source of light, such as a first laser, is accompanied by an optical hazard avoidance device, such as a second laser, that stimulates a voluntary, involuntary, or both a voluntary and an involuntary responses, either physiological or behavioral or both physiological and behavioral, within one or more hazard zones, such as by inducing gaze aversion within the viewer. Physiological responses are reflexes, often involuntary, of a single subject that mitigate or avoid damage, such as blinking, flinching, pupil contraction, closing of the eyes, averting a gaze, ducking and the like. Behavioral responses are individual or group responses that mitigate or avoid damage by limiting exposure to potential hazards by changing the behavior of an individual or group, such as by moving farther away, shielding of eyes, looking away without looking back, dispersing of a crowd and the like.

In one example, an optical hazard, such as a powerful source of light that is not visible, is combined with an optical hazard avoidance device comprising a visible light source, such as a light emitting diode and/or laser light source. For example, both a visible LED light source and a visible laser light source may be combined in an optical hazard avoidance device. The LED light source may stimulate a physiological or behavioral response within a short distance from the optical hazard. The visible laser source may stimulate a physiological response at longer ranges, out to at least the hazard zone of the optical hazard, for example. In one example, the visible LED light source causes an avoidance response within zero to ten meters from the optical hazard, while the visible laser light source causes an aversion of gaze or a blink response at a much greater distance. In one method, the LED light source is operated to warn any person or animal within a short range of the optical hazard to shield its eyes or to avert its gaze or to exhibit other physiological or behavioral responses, and the visible laser light source commences prior to the operation of an optical hazard for a short duration such that any viewer within a hazard zone blinks or averts the viewer's eyes prior to and during the illumination of a down range target or other object by the optical hazard, such as a laser range finder or laser used in a detection system. This can be repeated for each pulse of a pulsed optical hazard, if necessary. For a continuous operation of an optical hazard, the optical hazard avoidance device may be operated continuously or in a pulsed mode, stimulating rapid blinking and/or averting a gaze of any viewer down range within the hazard zone. The optical hazard avoidance device at least puts the viewer on notice of an optical hazard, which would not be apparent if the optical hazard comprising a source of light that is not visible, such as a laser operating in the infrared, ultraviolet or microwave ranges, for example.

The optical hazard avoidance device may be a system that stimulates either or both of a voluntary or involuntary response without exposing the subject to a dangerous level of light, itself. The system may include other components such as multiple light sources, range finders and lock outs to avoid use of the device if a person or animal is located within a certain range from the optical hazard avoidance device or to lock out the optical hazard until the person or animal moves away from the optical hazard, for example.

In one example, an optical hazard avoidance device ("OHAD") flashes in a pulse of intense, visible light that causes a viewer of the OHAD to involuntarily blink. The pulse may be repeated or may extend for an entire duration of exposure from an optical hazard, such as laser beam. A method of using the OHAD in conjunction with a high power laser light source may permit a higher power beam to be used than otherwise be permitted. The high power laser light source could exceed the safety threshold for duration and intensity of the laser beam, because any person down range would be protected by the OHAD stimulating an avoidance response during the entire time that the high power laser light source is operating.

In alternatives, additional or other types of energy may be emitted from the OHAD, such as sonic or thermal energy. For example, a directed sound amplifier could cause a sudden loud noise to be directed down range along the line of sight of an optical hazard, stimulating a flinching, ducking or other avoidance response. In addition, microwaves may induce a burning sensation on exposed skin that can stimulate a physiological or behavioral avoidance response. In one example, a combination of these and light are used to stimulate an avoidance response.

ANSI Z136.1-2007 defines the blink reflex as the involuntary closure of the eyes as a result of stimulation by an external event such as . . . a bright flash," which is adopted herein as the definition of the blink reflex. In ANSI Z136.1-2007, "the ocular aversion response for a bright flash of light is assumed to limit the exposure of a specific retinal area to 0.25 seconds or less," because the standard assumes that the optical hazard and the bright flash of light are caused by one and the same light source. Thus, a bright flash of light that would involuntarily stimulate the blink reflex is limited to a threshold intensity level along its path not greater than a level that would cause ocular damage in 0.25 seconds or longer. A method of optical hazard avoidance using an optical hazard avoidance device can allow the intensity of a laser light source greater than that allowed in the standard, because the method uses the device to stimulate a blink reflex up to 0.25 seconds before the operation of the laser light source. In one example, the laser light source is a pulsed laser of a short duration, preventing any exposure of a person down range due to the involuntary blink response stimulated by using the optical hazard avoidance device in the method of optical hazard avoidance. In one example, the optical hazard avoidance device is a flash that starts 0.25 seconds before operation of a hazardous laser light source, and the pulse of the flash of the device continues until the pulse of the hazardous laser light source is completed. In this way, the optical hazard avoidance device prevents the viewing of the pulsed, hazardous light source by a single blink reflex of any person down range. In another method, the optical hazard avoidance device is a rapidly pulsed light source that flashes on and off during the operation of a hazardous laser light source, reducing the exposure of any person down range by causing repeated, involuntary blink reflexes and an aversion response.

BRIEF DESCRIPTION OF THE DRAWINGS

FIGS. 8-8C illustrate schematic examples of superimposed beams and cross-sections taken along the superimposed beams at different distances.

DETAILED DESCRIPTION

Figure 1:
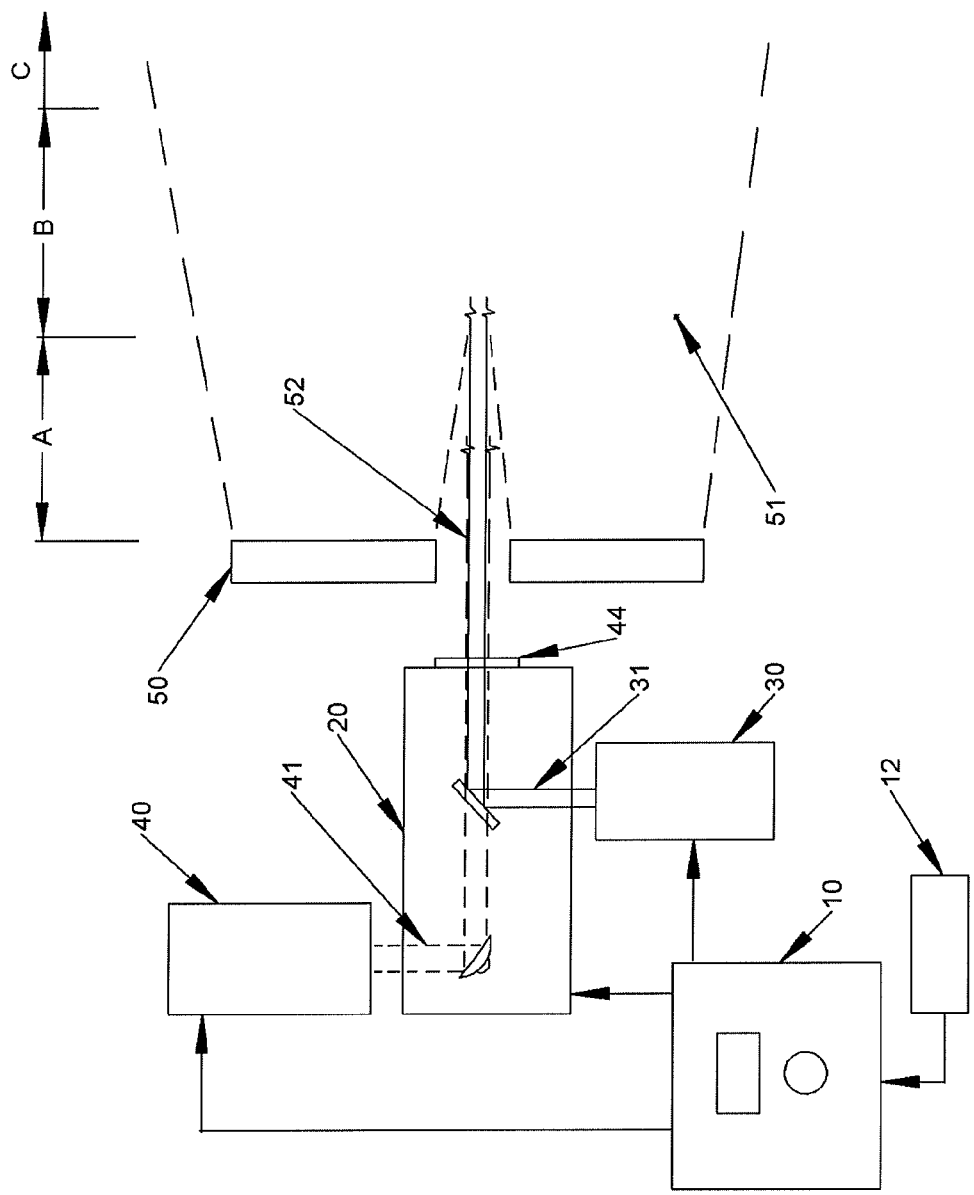
FIG. 1 illustrates an example of a system including an optical hazard avoidance device.

FIG. 1 illustrates an example of a system including an optical hazard avoidance device (OHAD). The system includes a power supply 12, which provides or directs power to a controller 10 that controls the operation of components of an OHAD including a laser 40 and an array 50, such as an array of speakers, light emitting diodes, microwaves or other sources of radiation. A potential optical hazard 30 is represented by a second laser. The first laser 40 and the second laser 30 emit beams 41, 31 of radiation, which may be visible light or radiation that is not in the visible spectrum, which may be referred to as light herein, even if the radiation is in the non-visible spectrum, such as infrared or ultraviolet. Optics 20 is capable of superimposing the first beam 41 along the same path as the second beam 31, such that the OHAD laser 40 follows the same path and is reflected, refracted and otherwise scattered similarly to the first beam 31. The array 50 is arranged as a concentric annulus around the second beam 31, which passes through a hole 52 in the array 50, and the array 50 provides a more highly divergent radiation 51 than the second beam 31. The radiation 51 of the array 50 converges at a first distance A from the array 50. In one example, the array 50 has an intensity of light that is eye safe but is capable of stimulating an avoidance response from first distance A to a second distance B.

In one example, the first laser 40 of the OHAD is eye safe at least at the second distance B or nearer and is capable of stimulating an avoidance response, such as a blink reflex, to a third distance C, beyond which the beam 31 of the potential optical hazard 30 is sufficiently attenuated to be eye safe, according to the standards in ANSI Z136.1-2007, which is the applicable standard of eye safety for lasers in the United States, for example.

Figure 2:
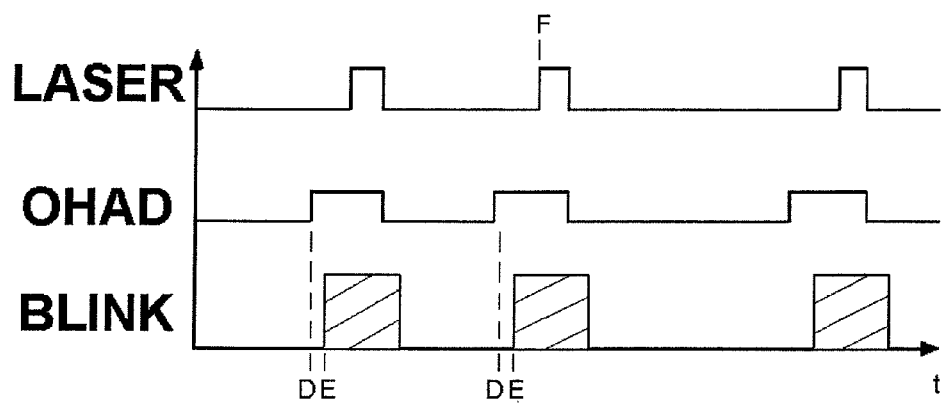
FIG. 2 illustrates a graph of an example of OHAD timing for stimulating a blink response.

FIG. 2 illustrates one example of timing used for controlling a light source, such as a laser, in an OHAD using a controller 10. The ordinate (x-axis) is time and the abscissa (y-coordinate) illustrates the comparative timings in FIGS. 2 and 3. In FIG. 2, the controller 10 activates the OHAD at a first time D, which stimulates a blink reflex at a second time E prior to the activation of an optical hazard, such as a laser, at a third time F for each pulse of the potentially hazardous source of radiation.

Figure 3:
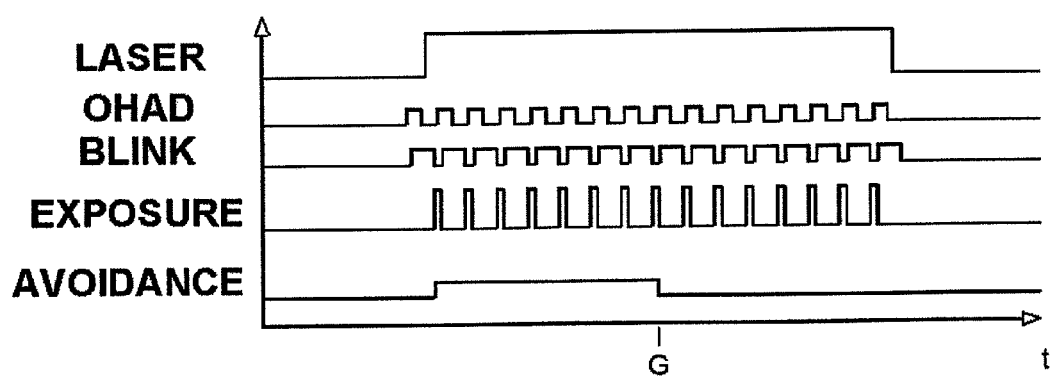
FIG. 3 illustrates a graph of another example of OHAD timing for stimulating a blink response.

FIG. 3 illustrates an alternative example for timing of an OHAD. In this example, a controller 10 repeatedly flashes the OHAD source or sources, stimulated a blink response (Blink) repeatedly during continuous operation of a potentially hazardous source of radiation, such as a laser (LASER), resulting in a much reduced exposure (Exposure). Furthermore, the repetition of the flashes could result in an avoidance response (Avoidance) that causes any person illuminated by the OHAD to avert the person's gaze from the direction of the potentially hazardous source of radiation, further reducing exposure, completely, at some point in time G.

A hazard region encompasses a limited area, volume or direction with respect to a person's field of view. Radiation may directly or indirectly cause a hazard in a region by directing radiation toward a person. Indirect exposure may be caused by scattering, reflecting or refracting of radiation, for example. An OHAD that follows the beam 31 of the hazardous radiation source has the advantage of being scattered, reflected and refracted similarly to the hazardous beam 31, provided that the wavelength is not too different from the source of the hazard; however, the beams 41, 51 of OHAD need not be co-linear with the beam 31 of the hazardous radiation source in order to stimulate an avoidance response in a hazard region. For example, the array 50 may provide a source of light that stimulates a blink response or repetition of a plurality of blink responses by flashing a plurality of light emitting diodes (LED's) within the array at the same time or at different times. In one example, the flashing of one set of LED's overlaps with the flashing of a following set of LED's such that flashing causes blink responses to occur very rapidly one after the other, leading any person in the particular hazard region to avert the person's gaze, entirely away from the potential hazard. Sound and heat may be generated in pulses or continuously to stimulate an aversion response, also, using an array 50.

In addition, the controller 10 may modulate the power, wavelength, divergence or other optical properties of the potentially hazardous source of radiation or the components of the OHAD in order to stimulate an avoidance response within a hazard region before and during the time the potentially hazardous source of radiation creates a hazard region. Aversion responses may include one or a combination of blink reflex, pupillary response, accommodation reflex, saccade or other involuntary responses, for example. Preferably, an aversion response will cause a person in a hazard region to redirect the person's gaze away from any potential hazard. Alternatively, the OHAD may limit the exposure or damage by altering the eye's susceptibility to ocular damage.

Any radiation in excess of a maximum permissible exposure within a nominal hazard zone may be mitigated or avoided entirely by using a method of optical hazard avoidance using an OHAD, even if a person within a nominal hazard zone otherwise would suffer ocular damage from line of sight exposure within the person's field of view. According to the standard a blink reflex occurs no later than 0.25 seconds after the OHAD stimulates the blink reflex; therefore, the time between activating the OHAD D and the blink reflex E may be 0.25 seconds or longer in FIG. 2, for example. In FIG. 2, the length of the pulse of the hazardous radiation source is less than the length of a blink, which protects any person within the hazard zone from ocular damage. For example, the hazardous source could be an Nd:YAG laser with a wavelength about 1064 nanometers, and the OHAD may include a laser beam of visible light with a wavelength of 532 nanometers generated using a harmonic crystal 44, illustrated in schematically in FIG. 1, in the path of the beam 31 of the hazardous source 30. In this example, a single laser 30 in combination with the controller 10 and the harmonic crystal 44 may provide the light for stimulating an avoidance response for the OHAD and the potentially hazardous radiation. Likewise, the same Nd:YAG laser might be used to generate a beam at 532 nanometers and the crystal could be used to generate a potentially hazardous beam at a wavelength of 266 nanometers, under the control of the controller 10.

Figure 4:
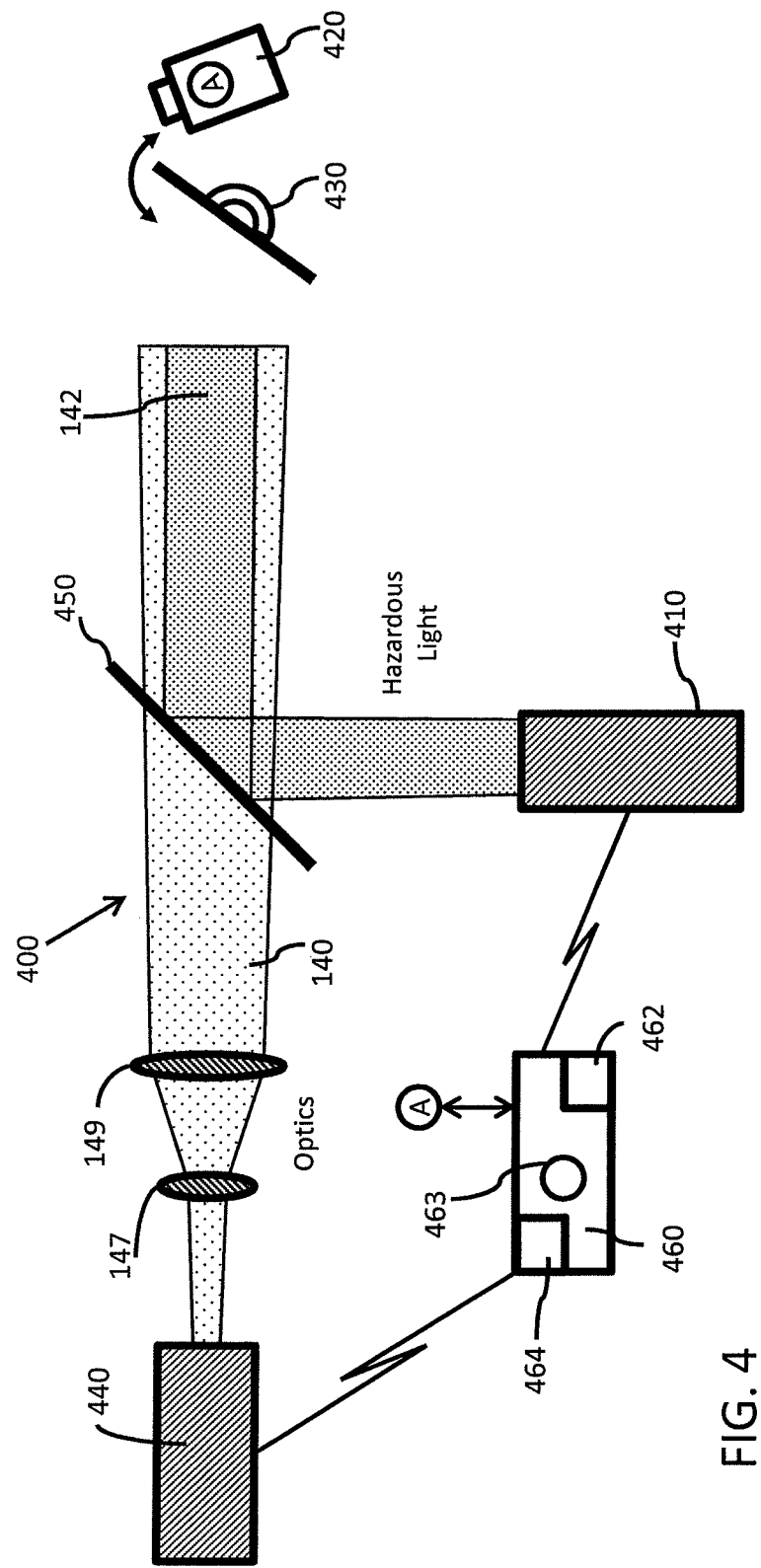
FIG. 4 illustrates another example of a system including an optical hazard avoidance device.
Figure 5:
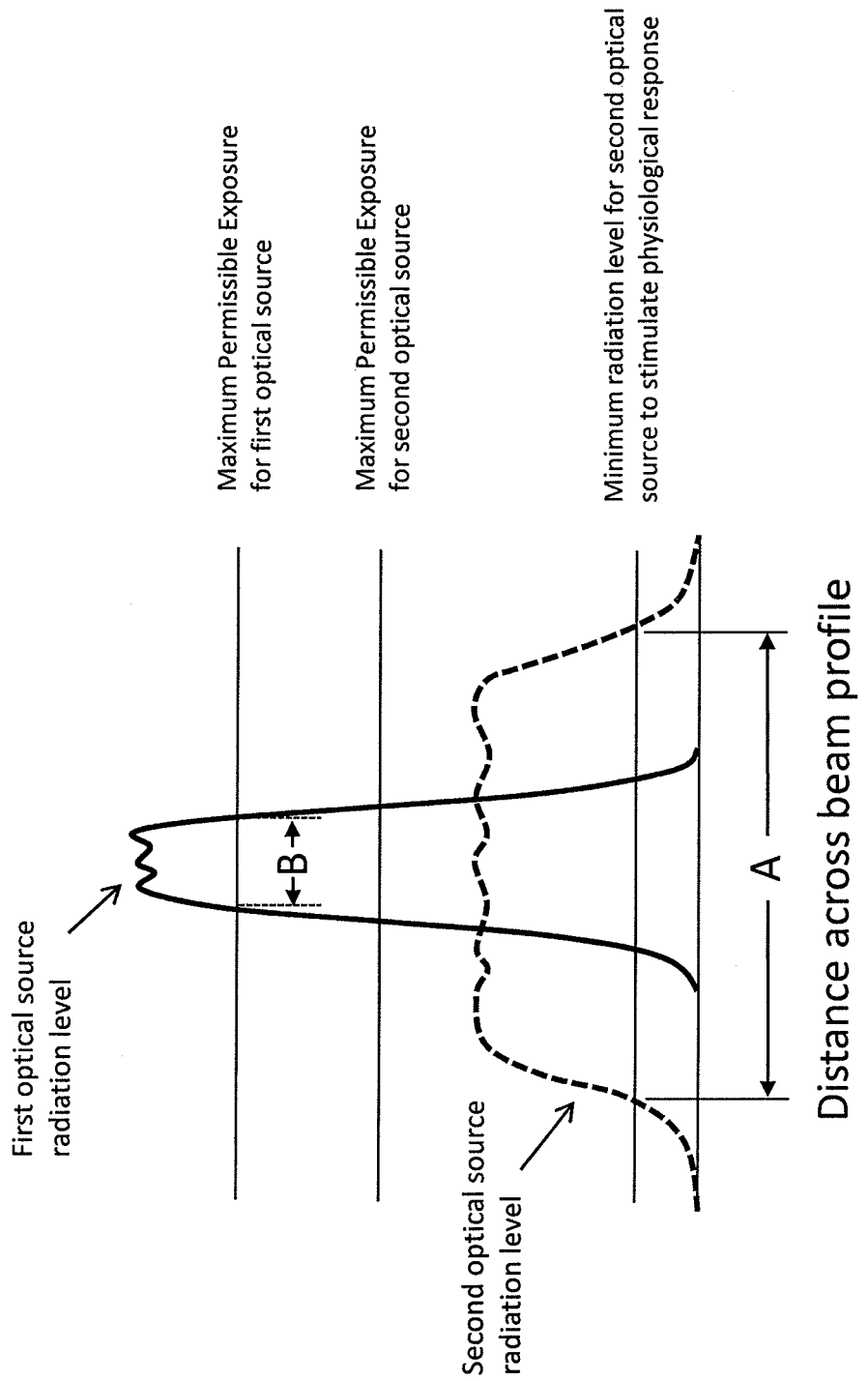
FIG. 5 is a schematic of two superimposed beams.

In one example, a standoff Raman Spectroscopy system is coupled with an OHAD capable of causing gaze aversion. For example, a TEPS system is disclosed in U.S. Pat. No. 8,125,627, the specification of which is incorporated herein in its entirety for the purpose of disclosing a TEPS system. FIG. 4 illustrates, schematically, a first optical source from a TEPS system that is combined with a second optical source of an OHAD, for example. For example, the OHAD emits a laser beam in the visible light spectrum that is capable of causing gaze aversion. An optical combiner is illustrated in the drawing, but other optical arrangements may be used to combine the two light sources, provided that the OHAD beam width is selected to cause gaze aversion in a width at least as wide as the portion of the beam width of the optical hazard that presents an optical hazard. The example in FIG. 4 is illustrative and an OHAD may comprise additional optical elements or alternative arrangements of optical elements. For example, FIG. 5 illustrates an intensity of a first optical source and a second optical source, which shows that the second optical source beam width is wider than the first optical beam width. In one example, the intensity of the second optical source is greater than the minimum radiation level required to stimulate a physiological response across a width A greater than the width B of the portion of the first optical source that exceeds the maximum permissible exposure for the first optical source. For example, the intensity of the second optical source may be greater than the critical response threshold over a particular range. The particular range may include all ranges over which the first optical source is hazardous or may include only a portion of the range over which the first optical source is hazardous. In one example, the particular range limits the optical hazard associated with the first optical source to a range very near first optical source, which limits the exclusion area required for firing of the first optical source.

Figure 6:
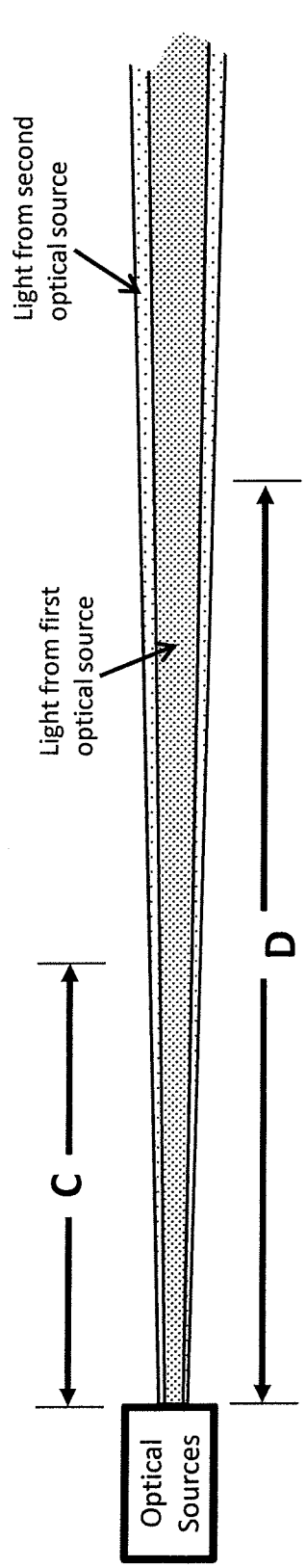
FIGS. 6 and 7 illustrate schematic examples of superimposed beams.
Figure 7:
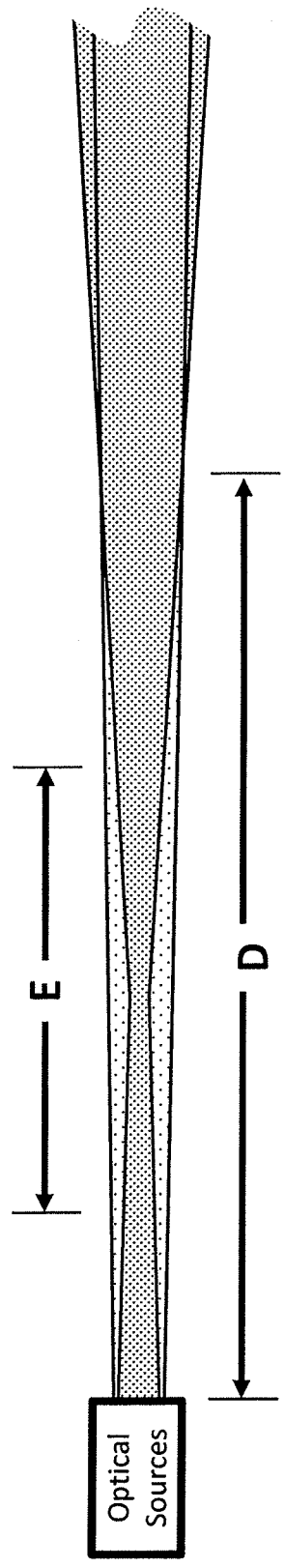

For example, FIG. 6 illustrates an example in which the first optical source is a diverging beam having a first optical hazard range C and the second optical source is a wider diverging beam creating a physiological response up to and including a range D greater than the optical hazard range C. In contrast to FIG. 6, FIG. 7 illustrates an optical hazard with a focal point down range that results in an intermediate optical hazard range E. For example, the range of the physiological response D is greater than, spans and includes the intermediate optical hazard range E. Alternatively, only a portion of the entire nominal hazard range is covered by the range of the physiological response(s) stimulated by an OHAD. In this alternative example, the risk associated with a nominal hazard may be nonetheless mitigated substantially. Alternatively, the physiological response(s) may be sufficient to entirely prevent ocular damage over entire range in which an optical hazard exists, when the first optical source is active. Alternatively, even though the physiological response is initiated, the physiological response may not entirely prevent ocular damage over the entire hazard range. Instead, the physiological response may mitigate the extent of ocular damage or may entirely prevent ocular damage only when combined with other techniques, such as an exclusionary zone. For example, the physiological response may mitigate damage causing such damage to be temporary, rather than permanent.

Figure 9:
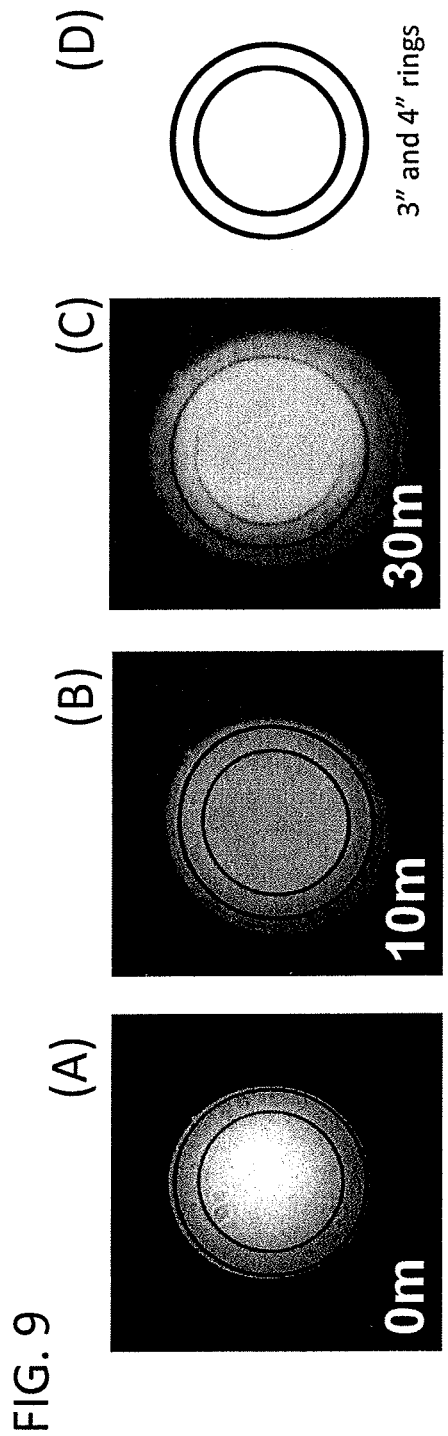
FIGS. 9A-9D illustrate examples of superimposed beams at various distances.

FIGS. 8-8C illustrate how beam width and range are both relevant in OHAD applications. FIG. 8 illustrates two diverging sources. FIG. 8A illustrates the beam widths and intensities at A'. FIG. 8B illustrates the beam widths and intensities at B'. FIG. 8C illustrates the beam widths and intensities at C'. At C', the intensity of the second source is less than that at which a physiological avoidance reaction would be stimulated, but the beam intensity of the first source is well within safe levels for the designed duration of exposure. At B', the first source is at the intensity that risks ocular damage of some type; however, the second source has an intensity and beam width that causes an optical hazard avoidance response, specifically, a physiological avoidance reaction, such as gaze aversion. The intensity of the second beam does not exceed its maximum permissible exposure (MPE) and the avoidance reaction is capable of limiting the exposure of the viewer to the first source, such that the viewer is not exposed to the maximum permissible exposure of the first source, even though the viewer would otherwise be in danger of ocular damage. At A', the MPE of the first source would be exceeded, except for the avoidance reaction induced by the second source, and the intensity of the second source remains in a safe range, less than the MPE of the second beam. For example, FIGS. 9A-C illustrate an OHAD that emits a bright light with a width as shown in the images, which is shown to extend beyond a 4-inch circle (i.e. 2.54 cm per inch). Light from the first source never presents an ocular hazard beyond the 4-inch circle over these ranges A', B' and C'.

Figure 10:
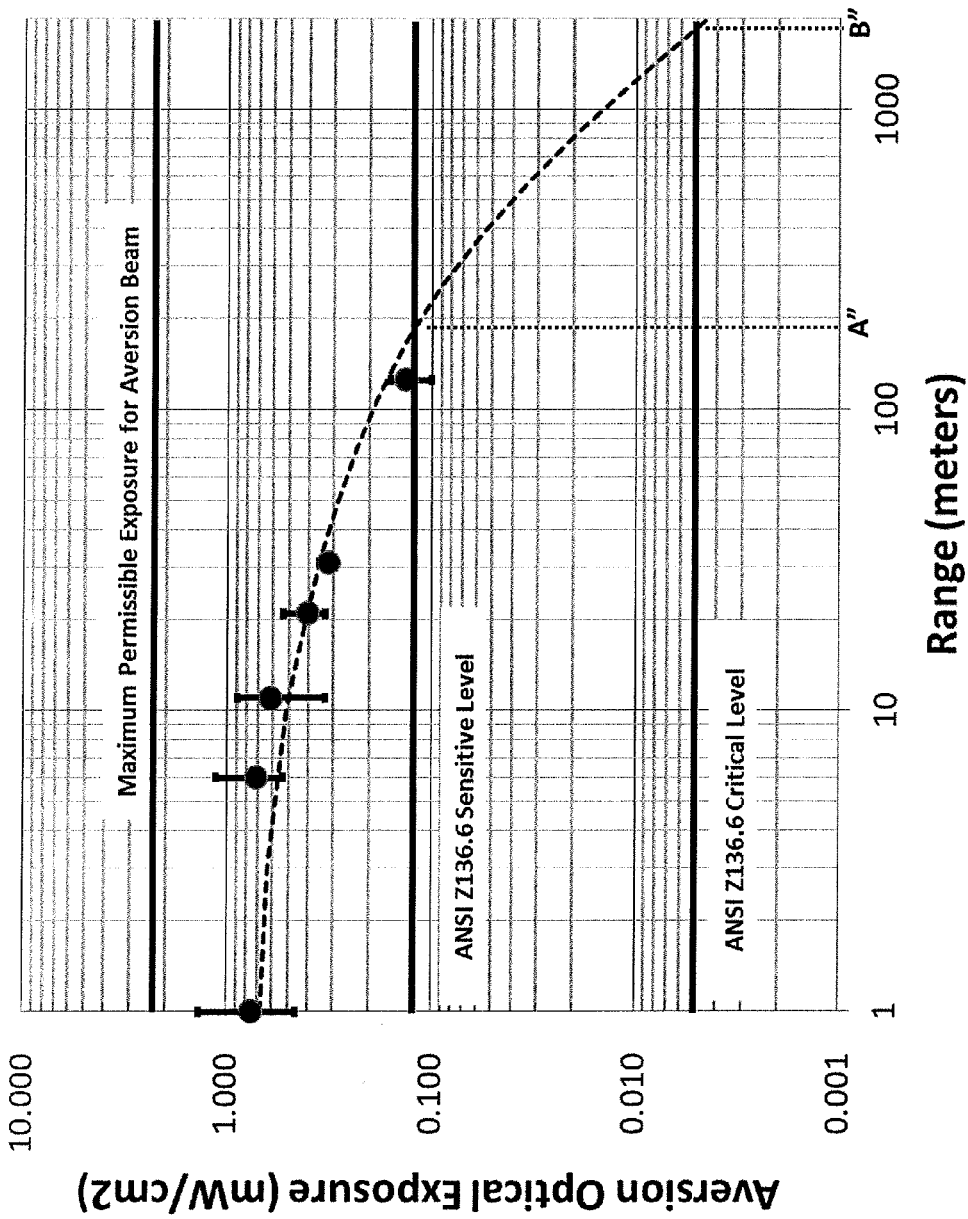
FIGS. 10-12 show illustrative graphs.
Figure 11:
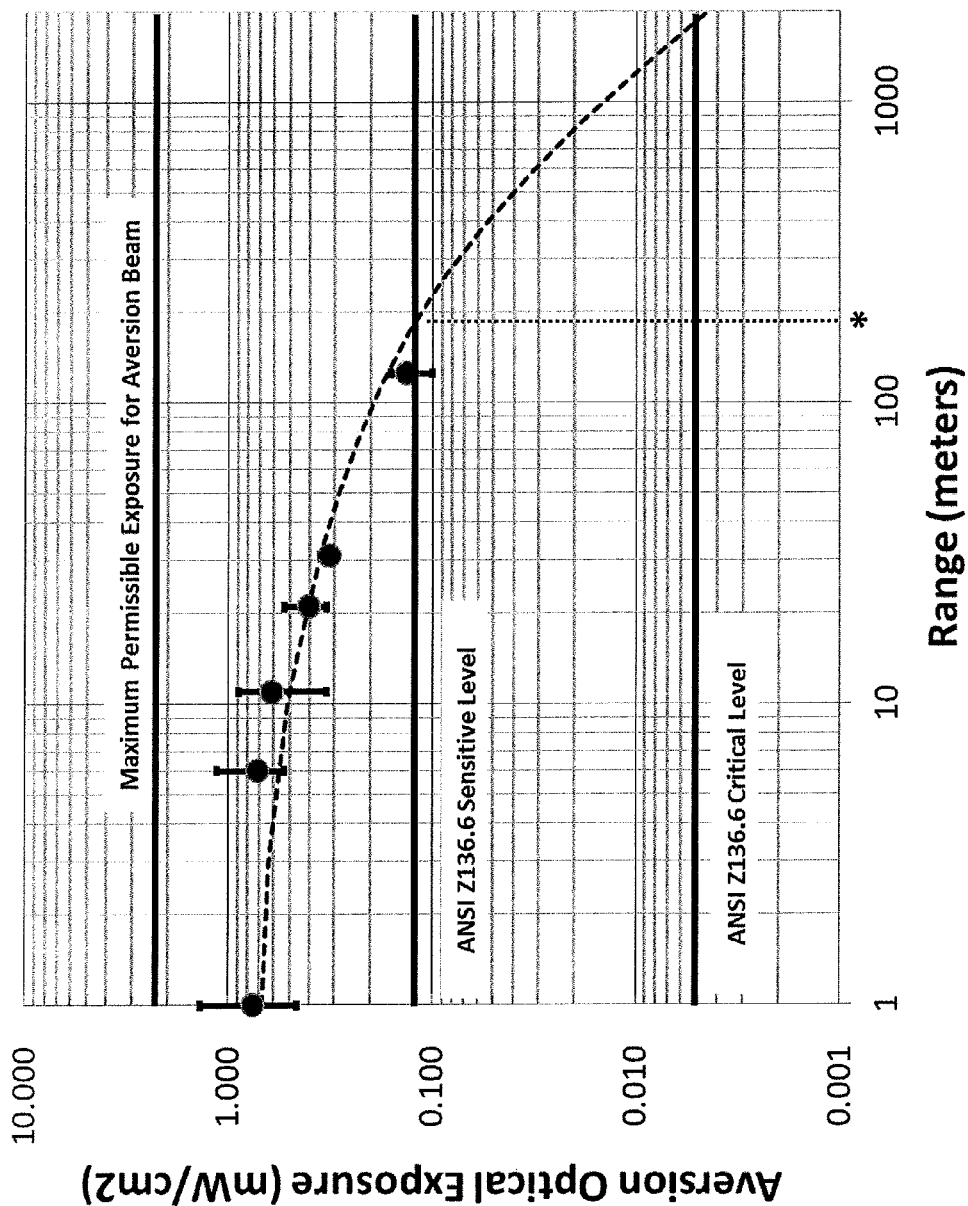
Figure 12:
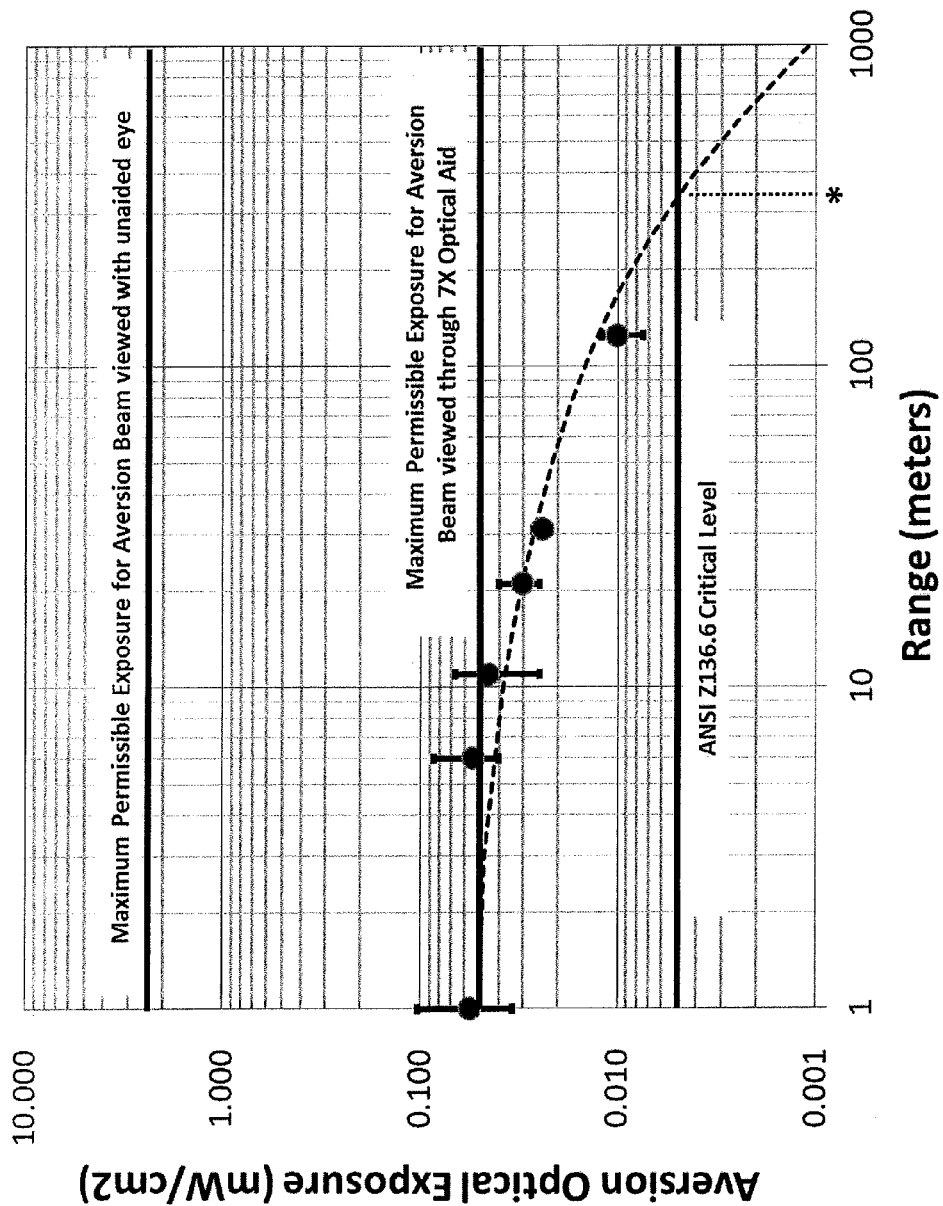
Figure 13:
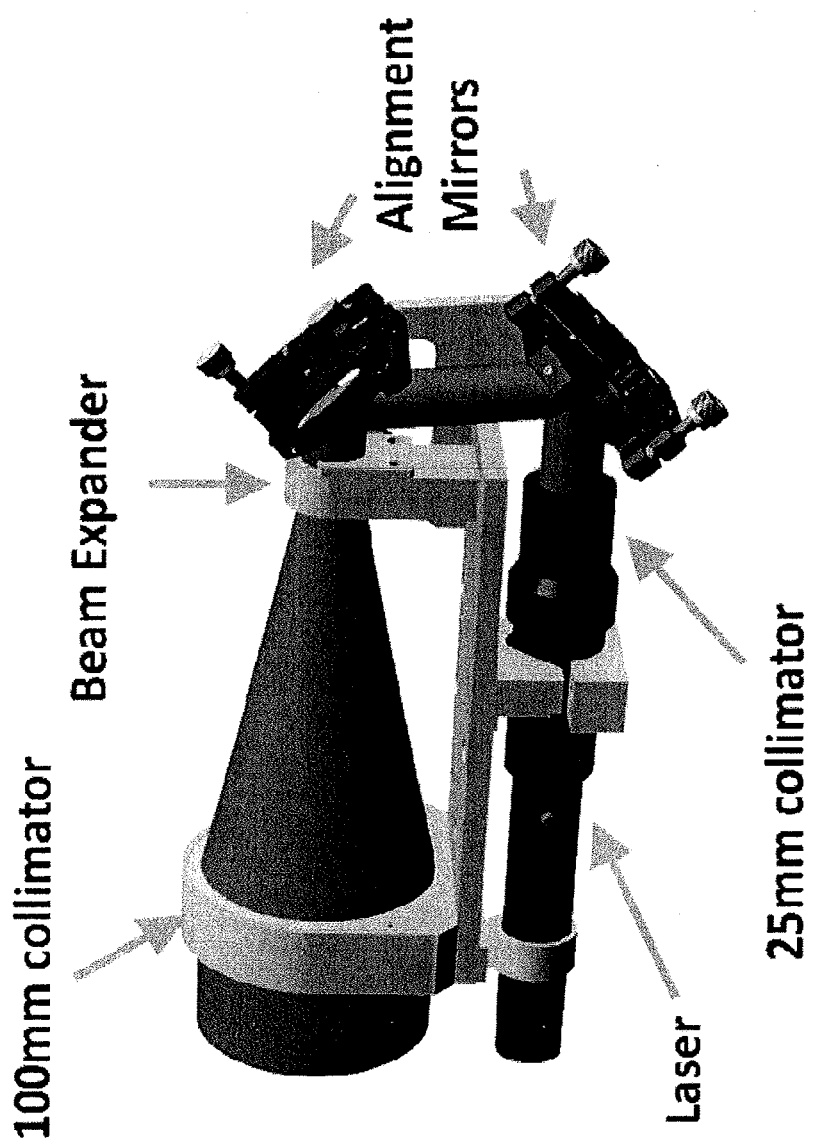
FIGS. 13-15 illustrate an example of a system including an optical hazard avoidance device.
Figure 14:
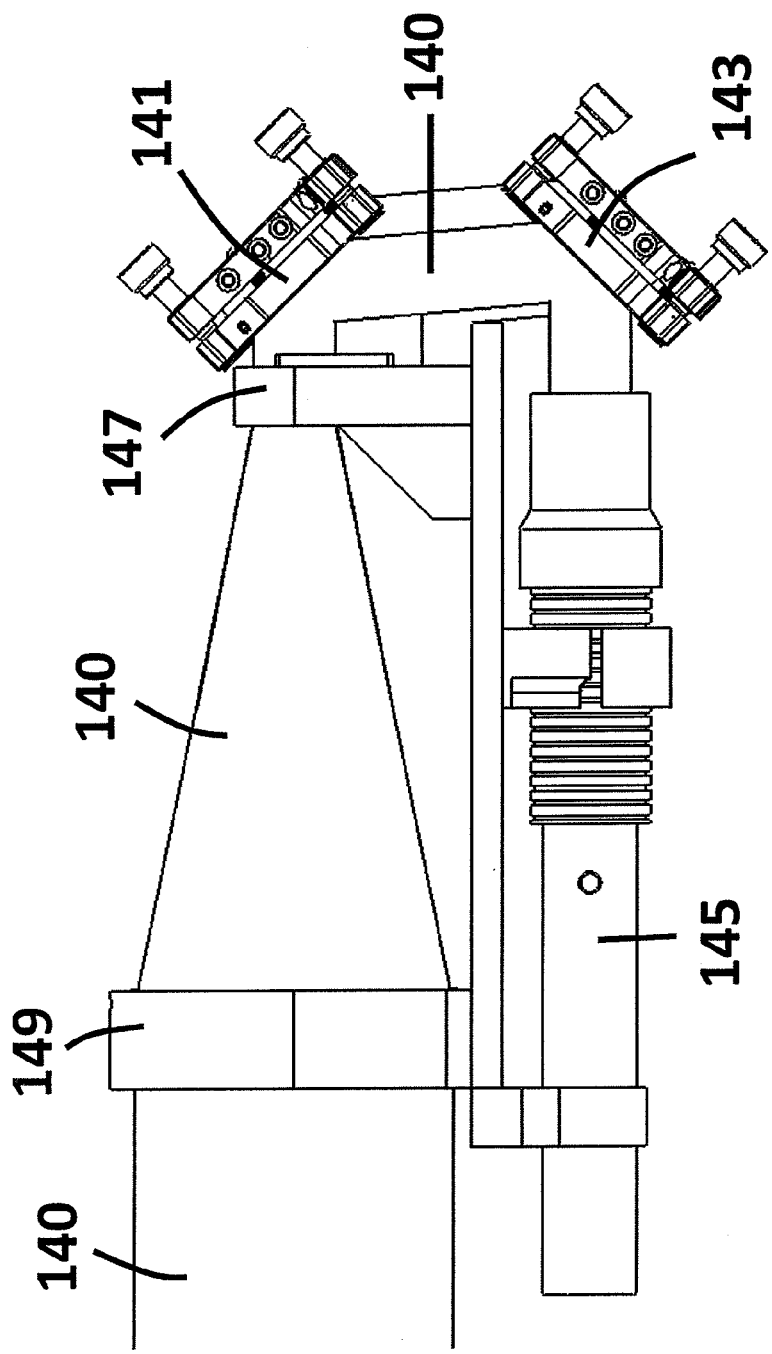
Figure 15:
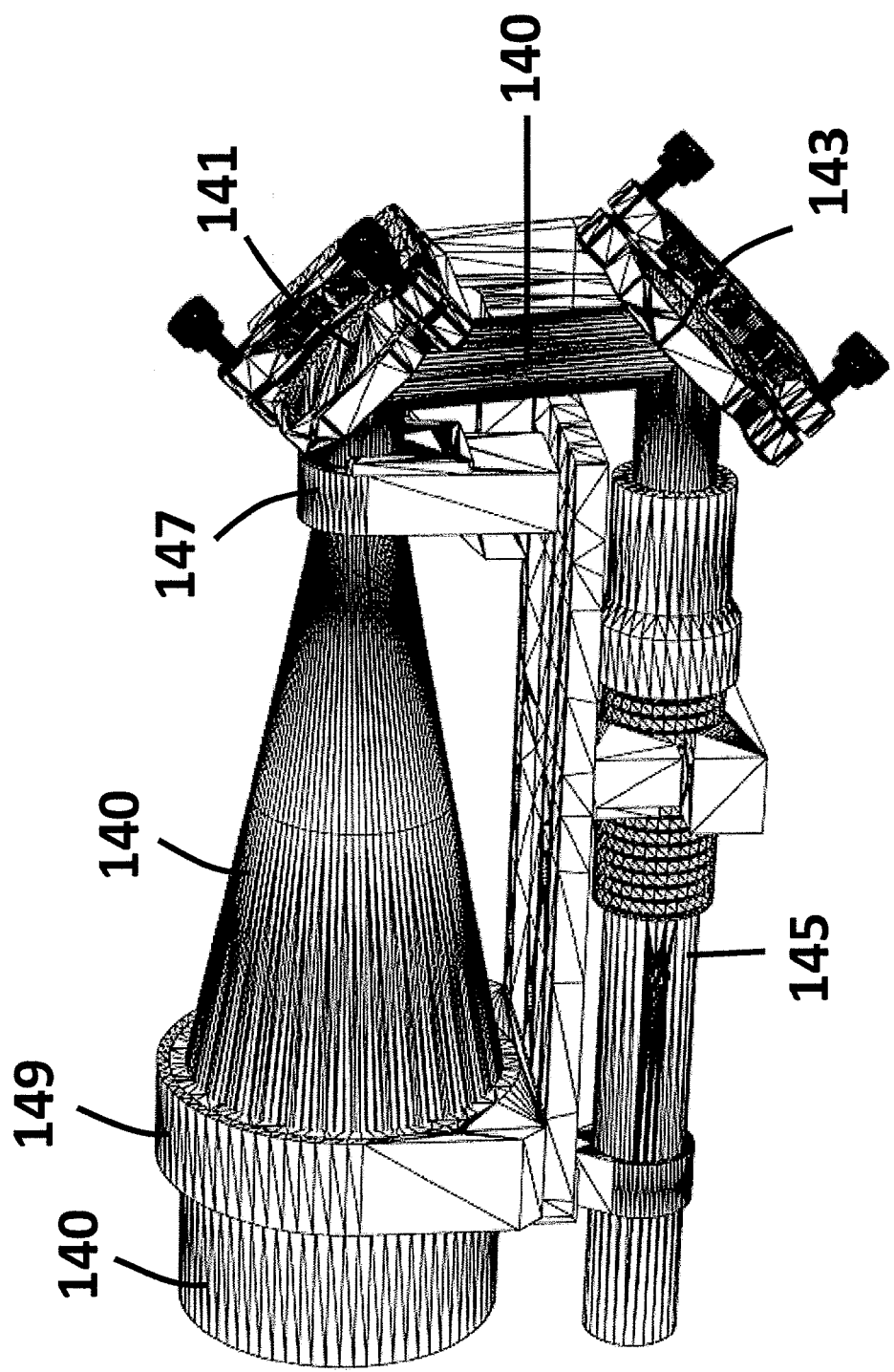

FIG. 10 illustrates an example of a graph of an aversion beam intensity versus distance in meters (i.e. range) for one example of a detector's aversion system using a 40 milliwatt continuous laser as the source of the aversion beam. FIG. 11 illustrates another example with the ANSI Z136.6 Sensitive Level superimposed on the graph, showing a range in meters for the aversion response induced by the aversion system. FIG. 12 illustrates another example, using a 3 milliwatt laser power output and superimposing maximum permissible exposure for the aversion beam when viewed through a 7× optical aid, such as binoculars. FIG. 13 illustrates an example of a laser used for generating an aversion beam mounted in an optical configuration including two alignment mirrors, a beam expander and a 100 mm beam collimator with the beams represented as shaded solids. FIG. 14 illustrates a side plan view of the example represented in FIG. 13. The laser 145 is directed toward a first alignment mirror 143 which directs the beam 140 toward a second alignment mirror 141. The second alignment mirror 141 redirects the beam 140 to a beam expander 147, which expands the width of the beam. A beam collimator 149 collimates the beam 140, which may continue to diverge over the range of the beam but not to the extent that it does between the beam expander and the beam collimator. The beam 140 then proceeds down range and provides for an aversion response, such as gaze aversion, for example. FIG. 15 illustrates a perspective view of the example illustrated in FIG. 14.

Figure 16:
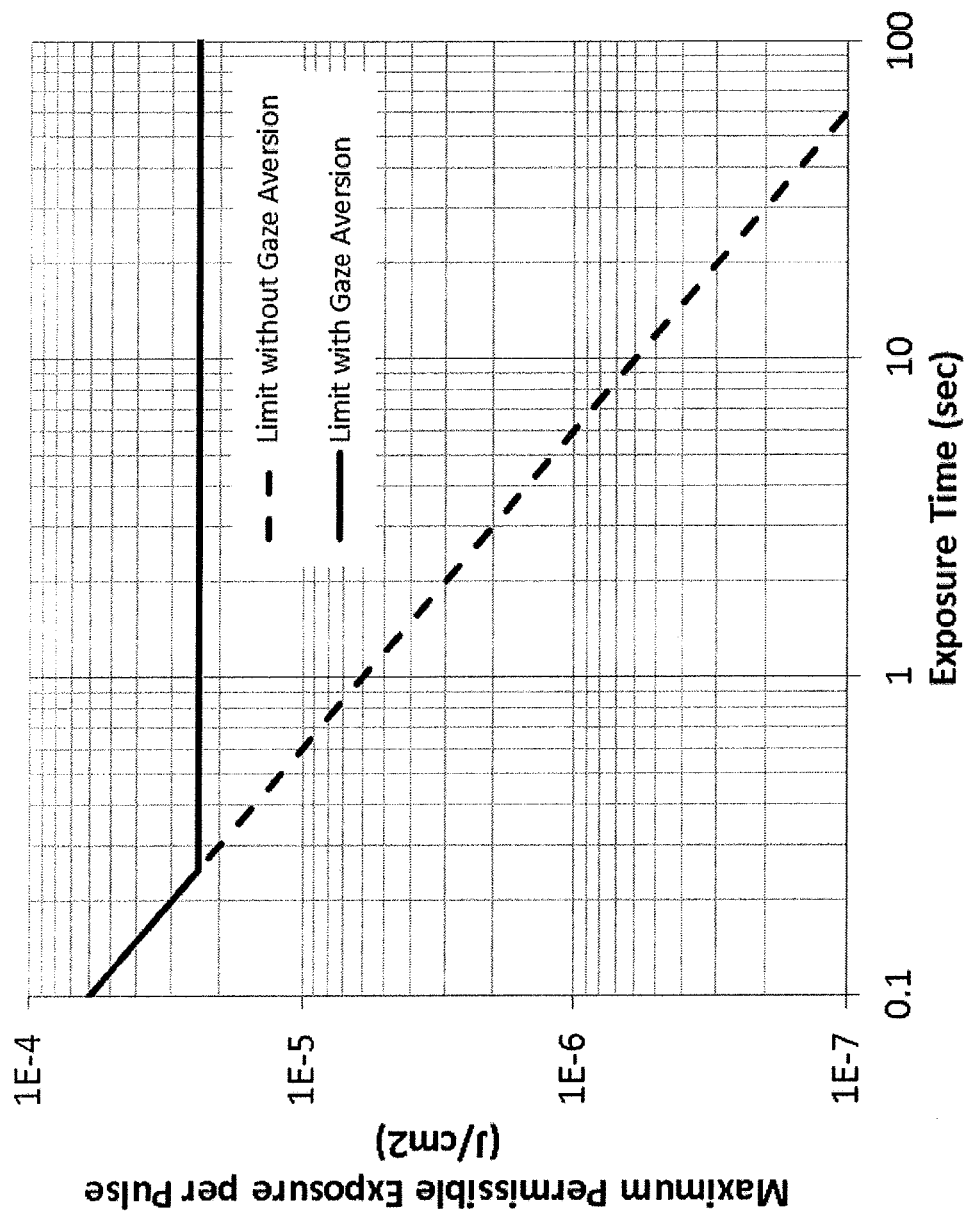
FIGS. 16-20 show illustrative graphs.
Figure 17:
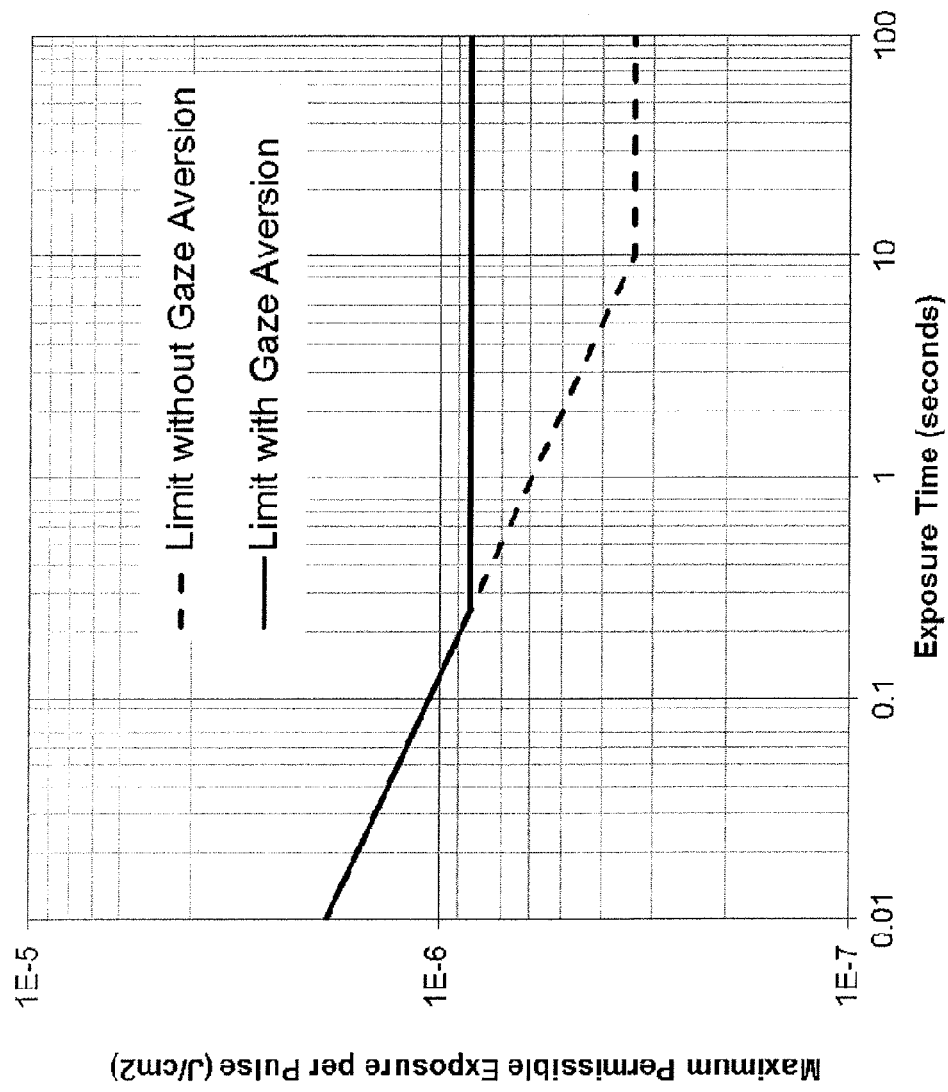

For example, FIGS. 16 and 17 illustrate examples of the maximum permissible exposure for ocular safety with gaze aversion (solid line) and without gaze aversion (dashed line) for an optical hazard comprising a 248 nanometer wavelength laser utilizing 500 pulses per second with a 20 nanosecond duration (FIG. 16) or a 1064 nanometer wavelength laser utilizing 5000 pulses per second with a 10 nanosecond pulse duration (FIG. 17). In both examples, the maximum permissible exposure per pulse for ocular safety is increased to a surprising and unexpected degree compared to the limit without the use of a gaze aversion source incorporated as an ocular safety device. In the example of the ultraviolet source, in FIG. 16, the permissible exposure per pulse is increased by more than an order of magnitude, allowing a much more powerful beam to be used in a device, such as a laser range finder or detector.

For example, it is believed, without being limiting in any way, that one example OHAD is capable of being implemented with a UV Raman trace chemical detector. In this example, the use of the OHAD limits the nominal hazard zone as defined in ANSI Z136.1 (NHZ) from 170 acres, making the detector impractical to use in any populated area, to just one-third of an acre, which is entirely manageable. In this example, a 248 nanometer wavelength UV Raman spectroscopy detector is utilized with a 15 centimeter aperture, 2 milliJoule pulse power, 300 Hz repetition rate for interrogating a target for 60 seconds from 40 meters away with a 1 square centimeter spot size. In this example, a UV Raman spectroscopy detector is entirely impractical for ocular-safe use within a populated area without OHAD and becomes completely practical when OHAD is utilized, making deep UV Raman usable as a detector in populated areas. This surprising and unexpected result combines synergistically a comparatively low power visible laser to induce an involuntary gaze aversion response with the UV Raman source for inducing detectable inelastic scattered light from a material, for example. In one example, a motion sensor is coupled with the OHAD and detector to prevent emission of either or both sources if movement is detected with the NHZ. The OHAD reduces the NHZ to a manageable area that is capable of being monitored by the motion sensor, for example. Utilizing the combination of a motion sensor and OHAD, there is no nominal optical hazard. Even if a motion sensor were used in the UV Raman system without OHAD, an optical hazard could exist outside of the range of practical motion sensors available for use with a UV Raman system.

Alternately, eye damage might not occur even though a nominal hazard exists. Nevertheless, a useful detector system would not meet safety standards for use. The nominal hazard calculations in the standard include safety factors and exposure at the MPE (a nominal optical hazard) is likely to not actually cause ocular damage. Nevertheless, a device including an optical source exceeding MPE would be judged to raise a nominal optical hazard; therefore, such a device would not be approved for use. In contrast, by combining one or more OHAD, the device could be approved for use by avoiding a nominal optical hazard.

Figure 18:
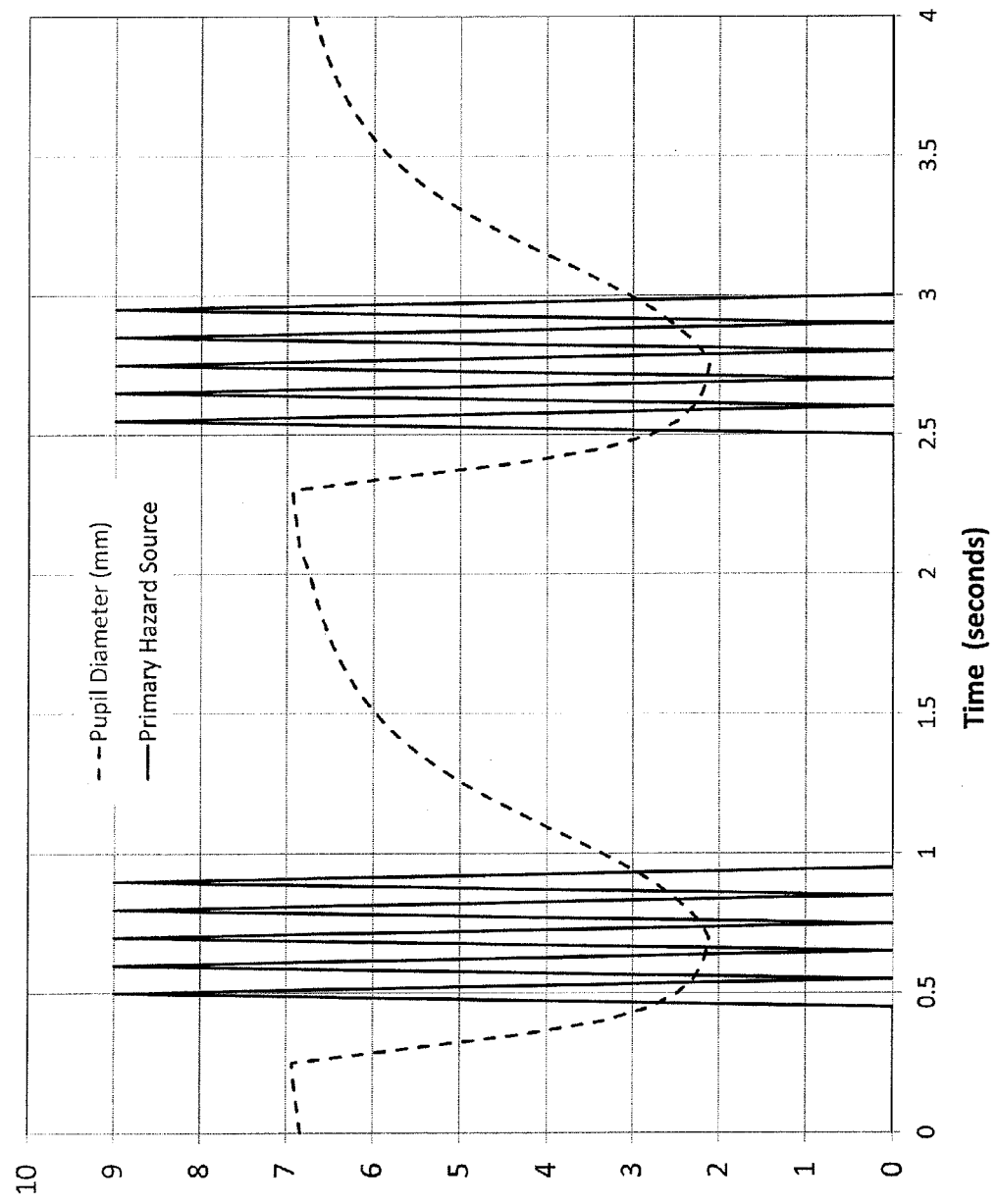
Figure 19:
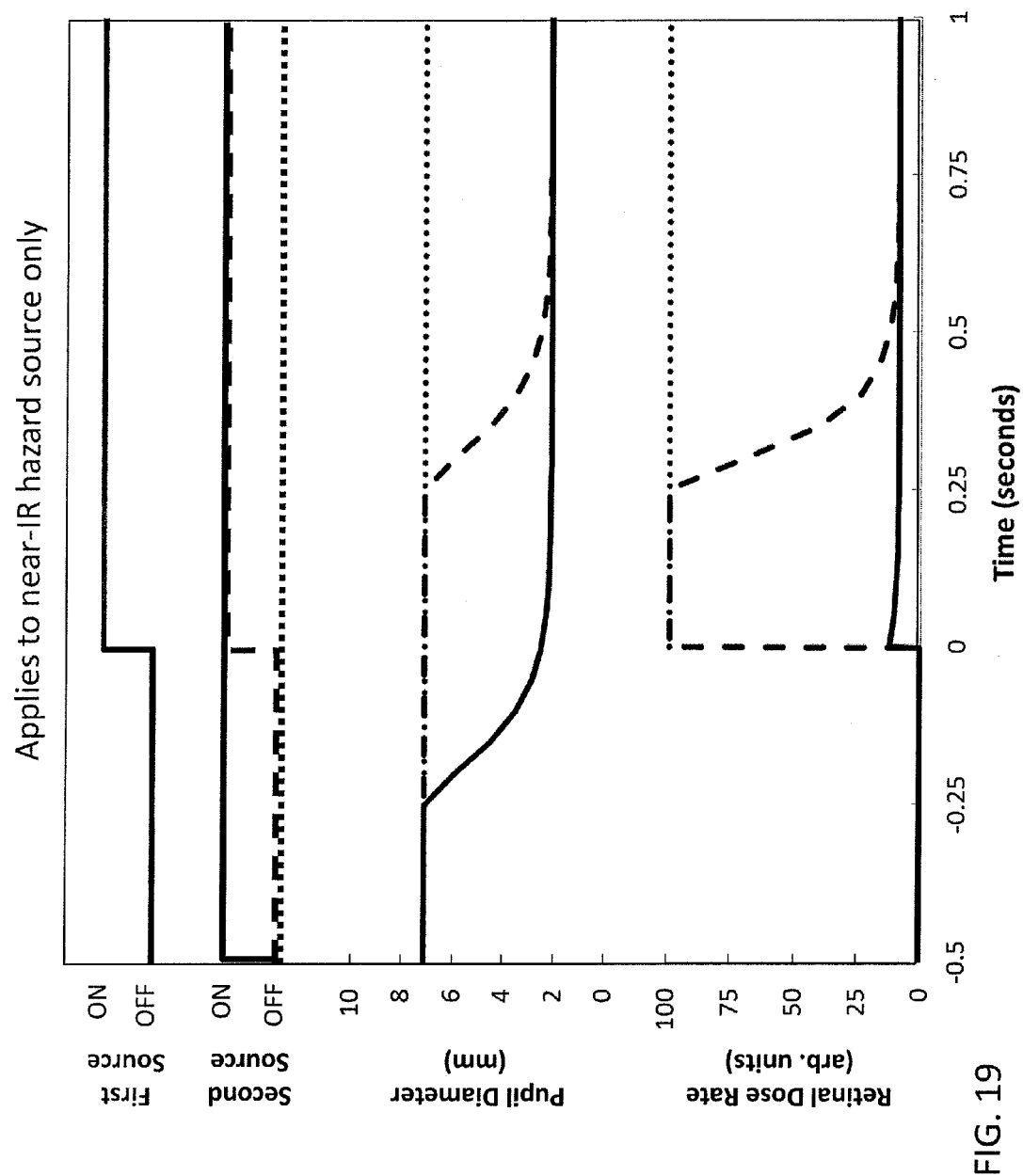
Figure 20:
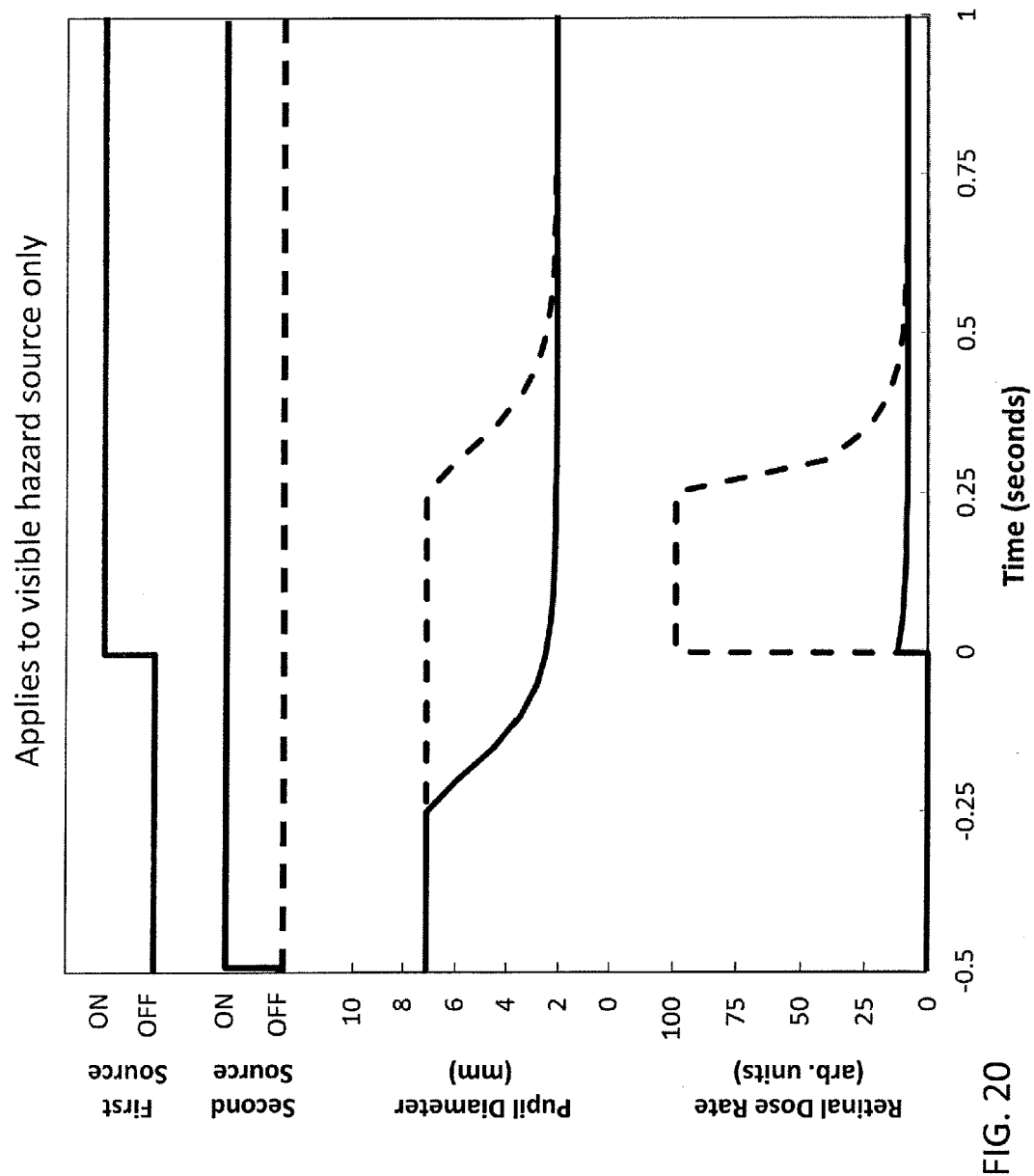

One example of an aversion response is pupil contraction. Pupil contraction response is a comparatively slow, involuntary response to an exposure to a bright light source, with a typical latency period of 100 to 300 milliseconds. In one example, a secondary source is selected with a wavelength and an intensity such that pupil contraction is initiated. For example, pupil contraction may be initiated prior to the initiation of a primary optical hazard such that a pupil contraction response is initiated prior to the initiation of the primary optical hazard or hazards, such as at 100 milliseconds, more preferably at 200 milliseconds, even more preferably at 250 milliseconds or 300 milliseconds, such that retinal exposure to a pulsed or continuous primary optical hazard or hazards does not exceed a nominal optical hazard. For example, a secondary source for initiating a pupil contraction response is limited to visible wavelengths, which fall within the range of wavelengths that would subject the retina to damage, also. Therefore, such an OHAD would be applicable only for protection against hazardous optical sources, such as lasers, comprising wavelengths in the visible (400-700 nm) or near-infrared (700-1400 nm). An OHAD utilizing a pupil contraction response and no other optical hazard avoidance response would provide no benefit for a primary optical hazard in the UV (less than 400 nm) or far-infrared (greater than 1400 nm), which could cause corneal damage regardless of pupil size. It may take up to about 2 seconds for a pupil to contract completely, although significant pupil contraction may occur within 0.5 seconds, even for a dark adapted eye. An OHAD strategy utilizing pupillary contraction response is illustrated in the graph of FIG. 18, for example, with a plurality of primary laser pulses timed to coincide with the pupillary contraction response induced by the OHAD visible optical source. In one example, a visible light OHAD is combined with a near-infrared primary laser. As is often assumed in calculating ocular hazards, such as in ANSI Z136.1, the viewer is assumed to have dark adapted pupils, with a nominal pupil diameter of 7 millimeters. In this example, it is assumed that no gaze aversion is stimulated. For example, as illustrated in FIG. 19, the visible light OHAD is triggered 0.5 seconds (solid lines) prior to the triggering of a near-infrared primary source, causing a viewer's pupil to contract prior to the triggering of the primary source. As a result, the retinal dose rate is dramatically reduced. If fired at the same time as the primary source (dashed lines), the OHAD still provides a reduced dose rate compared to no OHAD (dotted lines), but the dose rate during the first 0.5 seconds is increased in comparison. In comparison, a visible light OHAD with a visible light primary source is illustrated in the example of FIG. 20. It is assumed in FIG. 20 that the OHAD has a negligible impact on the overall retinal dose rate (i.e. low power compared to the primary source causing the optical hazard) and no gaze aversion response is induced, then the only benefit is gained by activating the OHAD before the primary source, which extends only for the pupil contraction time, which is assumed to be 0.5 seconds in the example). Under these conditions, the triggering of the OHAD at least 0.5 seconds prior to the primary source induces pupil contraction, which limits retinal dose rate.

In another example, blink aversion may be adopted by using an OHAD visible laser source to cause viewers to blink. The latency of the blink aversion response is thought to be 250 milliseconds and protects both the cornea and the retina from damage. Therefore, this response is suitable for all primary source wavelengths. In this example, the critical level for the OHAD is the level required to cause a nominal blink response, which might vary depending on ambient lighting conditions and to some degree on characteristics of the observer including medical conditions and use of legal and illegal drugs. This critical level for a blink response may be determined by characterizing the blink response to a secondary optical source emitting light in the visible spectrum. Alternatively, a blink response might be induced by a critical level or noise, directed or omnidirectional. Such a blink response may be initiated prior to the initiation of a primary optical hazard, such that the blink response substantially reduces or entirely eliminates exposure to the primary optical hazard, for example.

In yet another example, gaze aversion response is adopted by using an OHAD visible laser source to cause viewers to avert their gaze. Table 2 summarizes the benefits achieved from gaze aversion response. The benefits to ocular safety are surprisingly and unexpectedly great for the ultraviolet range of primary sources, which will reduce the exposure by 1200 times compared to the primary source without an OHAD utilizing the gaze aversion response, as illustrated in the example graph in FIG. 16, for example. There is no practical limit on the effective benefit of the gaze aversion response, which depends on the length of exposure to which the gaze is averted and the wavelength of the primary optical hazard. Longer exposures to a primary UV optical hazard can reduce the exposure by more than 1200 times, for example. The calculation of a comparative dose mitigation value has not been determined for this particular type of aversion response. Dose mitigation is defined herein as the dose with OHAD divided by the dose with OHAD in Table 2. Gaze aversion is already taken into consideration in standards for a primary laser within the visible spectrum, although a secondary optical source, such as a laser, could be used to reduce the latency, which is thought to be about 250 milliseconds. See Table 3 for a summary of exposure reduction by gaze aversion for a 5 nanosecond, pulsed laser having a 248 nanometer wavelength. Table 3 assumes that the OHAD is triggered at the same time as the primary laser, which explains why no mitigation factor up to 250 milliseconds is represented in the table. The scan times of a detector, which is taken as the duration of a primary optical hazard, in Table 3 are representative of the range of scan times utilized in UV Raman spectroscopy detectors, such as Checkpoint Explosives Detection System (CPEDS)[1], e.g. a dual-band ultra violet (UV) Raman standoff detection technology to detect trace residue from explosives chemicals and associated precursor materials with laser excitation wavelengths of 248 nanometers and 355 nanometers. Therefore, gaze aversion is a preferred optical hazard avoidance mechanism for an OHAD used in UV Raman spectroscopy detectors.

[1] CPEDS is a trademark of Alakai Defense Systems.

In one example, an OHAD combines a plurality of aversion responses. For example, pupil contraction response is combined with gaze aversion response or blink response is combined with gaze aversion response. For example, gaze aversion response provides 1200 times exposure for a UV primary source and 2.5 times exposure for near-infrared and far infrared primary sources, for the same duration of exposure, while pupil contraction response provides up to 12 times exposure for visible and near-infrared primary sources. In this example, the combined benefit for a UV primary source is 1200 times exposure, for visible primary source is up to 12 times exposure, for near-infrared is up to 30 times exposure (i.e. combining 2.5 times and 12 times), and for far-infrared is 2.5 times exposure. Furthermore, triggering of the OHAD 0.5 seconds prior to the primary source can reduce retinal dose rates in the visible and near-infrared spectrums. One or more aversion responses may be combined with a motion sensor or other interlocking device to increase ocular safety within an NHZ, if necessary. Also, a blink response may be utilized to reduce the exposure to both retina and cornea to nothing during the period when the eyelid is closed. By combining physiological responses as a result of an OHAD and other safety devices, damage that could be caused by a wide variety of optical hazards may be mitigated or avoided.

In one example, such as illustrated schematically in FIG. 4, a detector 400 comprises a first optical source 410, such as a primary laser, the first optical source having an optical hazard zone C, E, such as illustrated in FIGS. 6 and 7. The detector 400 comprises a sensor 420 for interrogating a signal from a substance stimulated by the first optical source 410, such as illustrated schematically in FIG. 4, for example. The detector 400 comprises a second optical source 440, such as a secondary laser beam 140, which may be emitted by a secondary laser. For example, the secondary laser beam 140 comprises a visible beam with an optical intensity selected for stimulating at least one physiological aversion or avoidance response in a human. The detector 400 comprises an optical system 140, 149 for directing the visible beam such that the visible beam is superimposed over a beam 142 emitted by the primary optical source 410 in at least a portion of the nominal hazard zone C,E of the primary optical source 410. The second optical source 440 may be capable of inducing the at least one physiological aversion or avoidance response in at least the portion of the nominal hazard zone of the primary laser, such that optical exposure to the beam emitted by the primary optical source 410 is mitigated or eliminated by the at least one physiological aversion or avoidance response stimulated in humans by the second optical source 440. For example, the beam 142 of the primary laser comprises emitted energy having an ultra-violet wavelength, such that no visible light is emitted by the primary optical source 410 and no physiological aversion or avoidance response is stimulated by the primary optical source 410. In one example, the beam of the primary optical source 410 includes one or more lasers and comprises emitted energy comprising dual-band ultra-violet wavelengths. The sensor and primary laser may provide a system for Raman standoff detection such that trace residue from chemicals produce a signal when exposed to the dual-band ultra-violet wavelengths, for example. The dual-band ultra-violet wavelengths may include emitted energy at wavelengths of 248 nanometers and 355 nanometers, for example. In one example, the optical system includes a first mirror 143 for redirecting the visible beam from the second optical source 440 and a second mirror 141 for redirecting the visible beam redirected by the first mirror 143, such as illustrated in FIGS. 13-15, for example. The optical system may include a beam expander 147, and the visible beam from the second mirror 141 may be directed through the beam expander 147, such that the beam diverges. After the visible beam is directed through the beam expander 147, the visible beam may be directed through a beam collimator 149, such that the diverging visible beam becomes more collimated, such that the effective width A of the collimated beam 140 is greater than the nominal hazard width B of the beam 142 of the primary optical source 410, as illustrated in FIGS. 4-5 and 13-15, for example.

The optical system may include an optical combiner 450, such as illustrated schematically in FIG. 4, which may be disposed after the beam collimator 149, for example, whereby the visible beam 140 is superimposed over the beam 142 emitted by the primary optical source 410 in at least a portion of the optical hazard zone of the beam 142 of the primary optical source 410. The optical system may include beam targeting optics 430, such as an adjustable targeting mirror, wherein the beam targeting optics 430 are capable of redirecting both the visible beam 140 of the secondary optical source 440 and the beam 142 of the primary optical source 410 toward a target (not shown) at a distance from the detector 400.

In one example, a time delay circuit 462 is included in a controller 460, which may be provided as an interlocking device, such that triggering of the detector delays for a delay time or prevents any initiation of the beam 142 emitted by the primary optical source 410. For example, the delay time may delay the primary optical source until after the initiation of the visible beam 140 of the second optical source 440. In one example, a delay of 100 millisecond, 200 milliseconds, 250 milliseconds or 300 milliseconds may be selected. For example, a sensor 420 may be integrated with the controller 460 to determine when or if the second optical source 440 is operational. If the sensor 420 does not detect the visible beam 142, or the visible beam 142 is detected at less than a threshold level, then the interlocking device may prevent the triggering of the primary optical source 410. In one example, a manual override 463 may be provided to override the interlocking device 464, as illustrated schematically in FIG. 4. Alternatively, the detector may not have a manual override.

A time delay circuit may be capable of delaying the initiation of the beam 142 emitted by the primary optical source 410 for at least 100 microseconds, for example, such that a pupil contraction or blink response may be initiated by the second source 440 prior to triggering the beam 142 of the primary optical source 410. In one example, the time delay circuit is capable of delaying the initiation of the beam emitted by the primary laser for at least 250 microseconds.

A method of implementing an optical hazard avoidance device may comprise a step of selecting an optical hazard avoidance system that combines a plurality of optical hazard avoidance responses in a human. The plurality of optical hazard avoidance responses selected from the optical hazard avoidance responses may consist of a blink response, a pupil contraction response and a gaze aversion response, for example. The method may include integrating the optical hazard avoidance system with a primary optical hazard, such that the optical hazard avoidance system mitigates or eliminates nominal risk of damage to a cornea or a retina of the human. By nominal risk of damage it should be understood that ANSI 2136.1-2007 is being used to determine whether there is a nominal risk of hazard within a nominal hazard zone (NHZ) when the primary optical hazard is operated absent the optical hazard avoidance device (OHAD), and the OHAD operates to mitigate or eliminate the nominal risk of hazard within at least a portion of the NHZ. The OHAD may provide a motion sensor or other sensor to prevent triggering of a primary optical hazard, when a human is detected within any residual NHZ, for example. By combining an optical hazard avoidance response with an interlocking device, the interlocking device is capable of preventing the firing of the primary optical hazard until the optical hazard avoidance device determines that the firing of the primary optical hazard is safe to humans. The control or controller 460 may include an interlocking device 464 and a time delay circuit 462 or the interlocking device may include the time delay circuit 462. Combining an interlocking device in an OHAD system may be used to prevent the firing of the primary optical hazard for a predetermined time delay period or for a time delay period selectable by a user of the OHAD. The time delay period may be at least 100 milliseconds, more preferably at least 250 milliseconds, if a blink response or pupil contraction response is required prior to the triggering of a primary optical hazard.

In one example, the step of combining includes monitoring a nominal hazard zone for the presence of a human and preventing the firing of the primary optical hazard until all humans are excluded from a residual nominal hazard zone. By residual nominal hazard zone, it is meant the nominal hazard zone, if one exists, after the mitigation by the OHAD of the nominal risk of damage from a primary optical hazard is taken into consideration. In an alternative example, a time delay is provided even after all humans are excluded from the residual nominal hazard zone. The step of monitoring may be automated by providing a sensor capable of detecting a human/animal within the residual nominal hazard zone, such as a motion sensor. For example, when a motion sensor has detected motion consistent with the presence of a human within the residual nominal hazard zone during a period prior to triggering of the primary optical hazard, the interlocking device prevents the firing of the primary optical hazard. When the interlocking device prevents the firing of the primary optical hazard, an audible or visible warning or alarm may be provided. For example, such a warning or alarm may indicate to the user of a detector that the nominal hazard zone is not clear and/or may provide a warning to any person in the residual nominal hazard zone.

One example of a method of using an optical hazard avoidance device to mitigate or eliminate a nominal optical hazard within a nominal hazard zone comprises selecting an optical hazard avoidance device having an intensity and wavelength of emitted radiation such that a plurality of optical hazard avoidance responses mitigate or eliminate a nominal optical hazard of a primary optical hazard. By integrating the OHAD with a primary optical hazard, an interlocking device may prevent triggering of the primary optical hazard until the plurality of optical hazard avoidance responses mitigate or eliminate the nominal optical hazard of the primary optical hazard, for example.

Other combinations and variations of the features of the examples of the invention disclosed are intended to be included within the scope of the invention, and the examples should not be taken as limiting any of the claims that eventually issue.

What is claimed is:

1. A detector comprising:
   a primary laser, the primary laser having an optical hazard zone;
   a sensor for interrogating a signal from a substance stimulated by the primary laser;
   a secondary laser emitting a visible beam for stimulating at least one aversion response;
   an optical system for directing the visible beam such that the visible beam is superimposed over a beam emitted by the primary laser in at least a portion of the optical hazard zone of the primary laser, wherein the secondary laser is capable of inducing the at least one aversion response in at least the portion of the optical hazard zone of the primary laser such that optical exposure to the beam emitted by the primary laser is mitigated by the at least one aversion response.

2. The detector of claim 1, wherein the beam of the primary laser comprises emitted energy having an ultra-violet wavelength.

3. The detector of claim 1, wherein the optical system includes a first mirror for redirecting the visible beam from the secondary laser and a second mirror for redirecting the visible beam redirected by the first mirror.

4. The detector of claim 1, further comprising a time delay circuit, such that triggering of the detector delays for a delay time any initiation of the beam emitted by the primary laser until after an initiation of the visible beam of the secondary laser.

5. The detector of claim 2, wherein the beam of the primary laser includes one or more lasers and the beam of the primary laser comprises emitted energy comprising dual-band ultra-violet wavelengths and the sensor and primary laser provide a system for Raman standoff detection such that trace residue from chemicals produce a signal when exposed to the dual-band ultra-violet wavelengths.

6. The detector of claim 5, wherein the dual-band ultra-violet wavelengths include emitted energy at wavelengths of 248 nanometers and 355 nanometers.

7. The detector of claim 3, wherein the optical system includes a beam expander, and the visible beam from the second mirror is directed through the beam expander, such that the beam diverges, and a beam collimator, wherein, after the visible beam is directed through the beam expander, the visible beam is directed through the beam collimator, such that the diverging visible beam becomes more collimated, such that an effective width of the collimated beam is greater than a nominal hazard width of the beam of the primary laser.

8. The detector of claim 7, wherein the optical system includes an optical combiner, whereby the visible beam is superimposed over the beam emitted by the primary laser in at least the portion of the optical hazard zone of the beam of the primary laser.

9. The detector of claim 8, wherein the optical system includes beam targeting optics, wherein the beam targeting optics are capable of redirecting both the visible beam of the secondary laser and the beam of the primary laser toward a target at a distance from the detector.

10. The detector of claim 4, wherein the time delay circuit is capable of delaying the initiation of the beam emitted by the primary laser for at least 100 microseconds.

11. The detector of claim 4, wherein the time delay circuit is capable of delaying the initiation of the beam emitted by the primary laser for at least 250 microseconds.

12. A method of implementing an optical hazard avoidance device for mitigating a primary optical hazard including a laser beam, comprising:
   selecting an optical hazard avoidance system capable of inducing an optical hazard avoidance response selected from the optical hazard avoidance responses consisting of blink response, pupil contraction response and gaze aversion response;
   integrating the optical hazard avoidance system with the laser beam of the primary optical hazard; and
   determining when nominal risk of damage to the cornea or the retina from the primary optical hazard exceeds permitted risks and allowing firing of the laser beam only when an interlocking device determines that risk of damage to the cornea or the retina of the human from the primary optical hazard is mitigated or eliminated by the optical hazard avoidance system.

13. The method of claim 12, wherein the step of selecting combines a plurality of optical hazard avoidance responses in a human, the plurality of optical hazard avoidance responses selected from the optical hazard avoidance responses consisting of blink response, pupil contraction response and gaze aversion response.

14. The method of claim 12, wherein the interlocking device includes a time delay circuit and the step of allowing firing prevents the firing of the primary optical hazard for a time delay period.

15. The method of claim 13, wherein the step of allowing firing includes monitoring a nominal hazard zone for presence of a human and preventing the firing of the primary optical hazard until all humans are excluded from the nominal hazard zone or the primary optical hazard within the nominal hazard zone is sufficiently mitigated or eliminated by the plurality of hazard avoidance responses.

16. The method of claim 14, wherein the time delay period is at least 100 milliseconds.

17. The method of claim 14, wherein the time delay period is at least 250 milliseconds.

18. The method of claim 15, wherein the step of monitoring is automated by providing a motion sensor, such that, when the motion sensor has detected motion consistent with the presence of a human within the nominal hazard zone during a period prior to triggering of the primary optical hazard, the interlocking device prevents the firing of the primary optical hazard.

19. The method of claim 18, wherein, when the interlocking device prevents the firing of the primary optical hazard, an audible or visible warning is provided.

20. A method of using an optical hazard avoidance device to mitigate or eliminate a nominal optical hazard within a nominal hazard zone, comprising:
   selecting an optical hazard avoidance device having an intensity and wavelength of emitted radiation such that at least one of a plurality of optical hazard avoidance responses mitigate or eliminate a nominal optical hazard of a primary optical hazard;
   integrating the optical hazard avoidance device with the primary optical hazard; and
   allowing triggering of the primary optical hazard only when the at least one of the plurality of optical hazard avoidance responses mitigate or eliminate the nominal optical hazard of the primary optical hazard.

21. The method of claim 20, wherein the step of selecting an optical hazard avoidance device includes a plurality of optical hazard avoidance responses; and the plurality of optical hazard avoidance mitigate or eliminate a nominal optical hazard of a primary optical hazard.

22. The method of claim 21, wherein the step of integrating includes selecting optics such that the optical hazard avoidance device has a diverging beam.

* * * * *